US012582308B2

(12) United States Patent
Ono

(10) Patent No.: US 12,582,308 B2
(45) Date of Patent: Mar. 24, 2026

(54) OPHTHALMIC APPARATUS AND METHOD OF CONTROLLING THE SAME

(71) Applicant: Topcon Corporation, Tokyo (JP)

(72) Inventor: Yusuke Ono, Kita-ku (JP)

(73) Assignee: TOPCON CORPORATION, Tokyo (JP)

( * ) Notice: Subject to any disclaimer, the term of this patent is extended or adjusted under 35 U.S.C. 154(b) by 382 days.

(21) Appl. No.: 18/031,904

(22) PCT Filed: Oct. 11, 2021

(86) PCT No.: PCT/JP2021/037527
§ 371 (c)(1),
(2) Date: Apr. 14, 2023

(87) PCT Pub. No.: WO2022/085501
PCT Pub. Date: Apr. 28, 2022

(65) Prior Publication Data
US 2023/0380680 A1 Nov. 30, 2023

(30) Foreign Application Priority Data
Oct. 22, 2020 (JP) ................................. 2020-177197

(51) Int. Cl.
*A61B 3/10* (2006.01)
*A61B 3/00* (2006.01)
(Continued)

(52) U.S. Cl.
CPC ............ *A61B 3/102* (2013.01); *A61B 3/0091* (2013.01); *A61B 3/117* (2013.01); *G06T 7/60* (2013.01); *G06T 2207/30041* (2013.01)

(58) Field of Classification Search
CPC ....... A61B 3/102; A61B 3/0091; A61B 3/117; G06T 7/60; G06T 2207/30041
(Continued)

(56) References Cited

U.S. PATENT DOCUMENTS

2012/0083667 A1 4/2012 Isogai et al.
2012/0140174 A1 6/2012 Hee et al.
(Continued)

FOREIGN PATENT DOCUMENTS

JP 2007-054423 A 3/2007
JP 2009-112431 A 5/2009
(Continued)

OTHER PUBLICATIONS

International Search Report and Written Opinion mailed on Dec. 14, 2021, received for PCT Application PCT/JP2021/037527, filed on Oct. 11, 2021, 9 pages including English Translation.
(Continued)

*Primary Examiner* — Mohammed A Hasan
(74) *Attorney, Agent, or Firm* — XSENSUS LLP

(57) ABSTRACT
An ophthalmic apparatus of according to an embodiment example includes a fixation target presenting unit, an OCT imager, a tilt information generator, and a controller. The fixation target presenting unit is configured to present a fixation target to a subject. The OCT imager is configured to apply optical coherence tomography (OCT) scanning to an anterior eye segment of a subject's eye to construct an image. The tilt information generator is configured to generate tilt information that represents a tilt state of the anterior eye segment depicted in the image. The controller is configured to control the fixation target presenting unit based on the tilt information.

17 Claims, 15 Drawing Sheets

(51) Int. Cl.
　　*A61B 3/117*　　　　(2006.01)
　　*G06T 7/60*　　　　(2017.01)

(58) Field of Classification Search
　　USPC ........................................................ 351/206
　　See application file for complete search history.

(56) References Cited

U.S. PATENT DOCUMENTS

| | | | |
|---|---|---|---|
| 2013/0050649 | A1 | 2/2013 | Juhasz et al. |
| 2013/0258280 | A1 | 10/2013 | Goto |
| 2013/0301008 | A1 | 11/2013 | Srivastava et al. |
| 2015/0085252 | A1 | 3/2015 | Fujimura et al. |
| 2015/0245765 | A1 | 9/2015 | Fujii et al. |
| 2015/0327762 | A1 | 11/2015 | Isogai et al. |
| 2015/0335479 | A1 | 11/2015 | Shibata et al. |
| 2016/0317029 | A1 | 11/2016 | Srivastava et al. |
| 2016/0345822 | A1 | 12/2016 | Fujimura et al. |
| 2017/0325675 | A1* | 11/2017 | Liu ..................... A61B 3/0025 |
| 2018/0153401 | A1* | 6/2018 | Strózyk .................. A61B 3/117 |
| 2019/0350455 | A1 | 11/2019 | Ono |
| 2021/0038071 | A1* | 2/2021 | Tatara ................... G06T 11/008 |
| 2021/0121061 | A1* | 4/2021 | Okamoto ............... A61B 3/117 |
| 2021/0196116 | A1 | 7/2021 | Yamaguchi et al. |
| 2021/0338076 | A1* | 11/2021 | Nakajima .............. A61B 3/107 |

FOREIGN PATENT DOCUMENTS

| | | | | |
|---|---|---|---|---|
| JP | 2011-147611 | A | | 8/2011 |
| JP | 2012-075640 | A | | 4/2012 |
| JP | 2013-226383 | A | | 11/2013 |
| JP | 2013-248376 | A | | 12/2013 |
| JP | 2014-500096 | A | | 1/2014 |
| JP | 2014-525286 | A | | 9/2014 |
| JP | 2015-043814 | A | | 3/2015 |
| JP | 2015-515894 | A | | 6/2015 |
| JP | 2015-160103 | A | | 9/2015 |
| JP | 2015195921 | A | * | 11/2015 |
| JP | 2019-118420 | A | | 7/2019 |
| JP | 2019-213740 | A | | 12/2019 |
| JP | 2020-151446 | A | | 9/2020 |

OTHER PUBLICATIONS

Office Action issued on Oct. 8, 2024, in corresponding Japanese patent Application No. 2020-177197, 9 pages.

Extended European search report issued on Aug. 26, 2024, in corresponding European patent Application No. 21882642.8, 7 pages.

Office Action issued on Jul. 8, 2025, in corresponding European patent Application No. 21882642.8, 4 pages.

Office Action issued on Aug. 5, 2025, in corresponding Japanese patent Application No. 2024-205181, 9 pages.

Office Action issued on Nov. 11, 2025, in corresponding Japanese patent Application No. 2024-205181, 10 pages.

* cited by examiner (B)

(A)

OPHTHALMIC APPARATUS AND METHOD OF CONTROLLING THE SAME

CROSS-REFERENCE TO RELATED APPLICATIONS

This application is a national stage (under 35 U.S.C. 371) of International Patent Application No. PCT/JP2021/037527, filed Oct. 11, 2021, claiming priority to Japanese Patent Application No. 2020-177197, filed Oct. 22, 2020, both of which are herein incorporated by reference in their entirety.

FIELD

The present disclosure relates generally to an ophthalmic apparatus, and a method of controlling the same.

BACKGROUND

Anterior eye segment analysis techniques using optical coherence tomography (OCT) are known, one of which is corner angle analysis that is conducted for diagnosis of glaucoma, especially, angle closure glaucoma (see, for example, Patent Documents 1 to 4 below).

In corner angle analysis, a calculation is performed based on an OCT image of an anterior eye segment to obtain a parameter related to a site referred to as a corner angle (anterior chamber corner angle) located between a cornea and an iris. The accuracy in the calculation of such a corner angle parameter can be deteriorated if the image of the anterior eye segment depicted in the OCT image is tilted. In particular, when the scan area is wide, the tilt and distortion of the image of the anterior eye segment increases, which greatly affects the accuracy of the corner angle parameter.

For example, in an ATA (angle-to-angle) scan, a B-scan (line scan) is applied to a cross section that passes through a corneal apex, the center of a pupil, or a point near the corneal apex of the center of a pupil, and two points on the corner angle having a substantially circular shape. In other words, in an ATA scan, a B-scan is applied to a cross section passing through a pair of opposing points on the corner angle having an approximately circular shape. If the image of the anterior eye segment in the OCT image obtained by the ATA scan is tilted, the image of the anterior eye segment is distorted, and the angle-to-angle distance and the angle of the corner angle cannot be accurately determined.

It should be noted that corner angle analysis is not the only anterior eye segment analysis technique that suffer from the effect of the tilting of an anterior eye segment image. In general, the effect is not small on any anterior eye segment analysis techniques that include assessment of morphology, form, or shape.

PATENT DOCUMENT 1: Japanese Unexamined Patent Application Publication No. 2011-147611

PATENT DOCUMENT 2: Japanese Unexamined Patent Application Publication No. 2013-226383

PATENT DOCUMENT 3: Japanese Unexamined Patent Application Publication (Translation of PCT Application) No. 2014-500096

PATENT DOCUMENT 4: Japanese Unexamined Patent Application Publication No. 2015-43814

BRIEF SUMMARY

An object of the present disclosure is to improve OCT anterior eye segment analysis.

An ophthalmic apparatus according to some aspect examples includes: a fixation target presenting unit configured to present a fixation target to a subject; an OCT imager configured to apply optical coherence tomography (OCT) scanning to an anterior eye segment of a subject's eye to construct an image; a tilt information generator configured to generate tilt information that represents a tilt state of the anterior eye segment depicted in the image; and a controller configured to control the fixation target presenting unit based on the tilt information.

In the ophthalmic apparatus according to some aspect examples, the controller is configured to control the fixation target presenting unit to move the fixation target.

In the ophthalmic apparatus according to some aspect examples, the controller is configured to control the fixation target presenting unit with referring to correspondence information generated in advance that represents correspondence between a tilt parameter representing a tilt state of an anterior eye segment in an image frame and a movement parameter of a fixation target.

In the ophthalmic apparatus according to some aspect examples, the tilt information includes a tilt angle with respect to a predetermined first reference direction in the image constructed by the OCT imager, the tilt parameter includes a tilt angle with respect to a predetermined second reference direction in the image frame, and the movement parameter includes a movement amount.

In the ophthalmic apparatus according to some aspect examples, the tilt angle included in the tilt parameter includes a predetermined unit angle with respect to the second reference direction, and the movement amount included in the movement parameter includes a unit movement amount corresponding to the unit angle.

In the ophthalmic apparatus according to some aspect examples, the correspondence information includes information that represents correspondence between a plurality of different tilt angles with respect to the second reference direction and a plurality of different movement amounts.

In the ophthalmic apparatus according to some aspect examples, the tilt information further includes a tilt direction with respect to the first reference direction, the tilt parameter further includes a tilt direction with respect to the second reference direction, and the movement parameter further includes a movement direction.

In the ophthalmic apparatus according to some aspect examples, the controller is configured to perform a control of the fixation target presenting unit, a control of the OCT imager, and a control of the tilt information generator in parallel, the control of the fixation target presenting unit being in order to move the fixation target, the control of the OCT imager being in order to sequentially construct an image while repetitively applying OCT scanning to the anterior eye segment, and the control of the tilt information generator being in order to sequentially generate tilt information from the image sequentially constructed by the OCT imager, and the controller is further configured to perform a control of the fixation target presenting unit to stop a movement of the fixation target in response to generation of tilt information that satisfies a predetermined condition.

In the ophthalmic apparatus according to some aspect examples, the tilt information includes a tilt angle with respect to a predetermined reference direction in the image, and the condition is a condition related to the tilt angle.

In the ophthalmic apparatus according to some aspect examples, the condition is that the tilt angle is smaller than a predetermined threshold value.

In the ophthalmic apparatus according to some aspect examples, the controller is configured to perform a control of the fixation target presenting unit through determining a movement direction of the fixation target based on one or more pieces of the tilt information sequentially generated by the tilt information generator from the image sequentially constructed by the OCT imager.

An ophthalmic apparatus according to some aspect examples includes: a fixation target presenting unit configured to present a fixation target to a subject; an OCT imager configured to apply optical coherence tomography (OCT) scanning to an anterior eye segment of a subject's eye to construct an image; a tilt information generator configured to generate tilt information that represents a tilt state of the anterior eye segment depicted in the image; an operation device configured to generate a signal upon receipt of an operation; and a controller configured to control the fixation target presenting unit based on the signal from the operation device and display information based on the tilt information on a display device.

In the ophthalmic apparatus according to some aspect examples, the information based on the tilt information includes one or more of: information representing a tilt angle with respect to a predetermined reference direction in the image, information representing a movement amount of the fixation target corresponding to the tilt angle, information representing a tilt direction with respect to the reference direction in the image, and information representing a movement direction of the fixation target corresponding to the tilt direction.

In the ophthalmic apparatus according to some aspect examples, the tilt information generator is configured to analyze the image constructed by the OCT imager to identify at least one feature point and perform generation of the tilt information based on the at least one feature point.

In the ophthalmic apparatus according to some aspect examples, the at least one feature point includes one or more of: a corner angle, an apex of an anterior surface of a crystalline lens, a corneal apex, and a point on an anterior surface of an iris.

In the ophthalmic apparatus according to some aspect examples, the OCT imager is configured to apply OCT scanning to a region that includes at least two points of the corner angle of the subject's eye and construct the image, and the tilt information generator is configured to identify the at least two points as the feature point and perform generation of the tilt information based on the at least two points.

In the ophthalmic apparatus according to some aspect examples, the OCT imager is configured to apply OCT scanning to a region that includes the apex of the anterior surface of the crystalline lens of the subject's eye and construct the image, and the tilt information generator is configured to identify the apex of the anterior surface of the crystalline lens as the feature point, calculate a gradient of the anterior surface of the crystalline lens at the apex of the anterior surface of the crystalline lens, and perform generation of the tilt information based on the gradient.

In the ophthalmic apparatus according to some aspect examples, the OCT imager is configured to apply OCT scanning to a region that includes the corneal apex of the subject's eye and construct the image, and the tilt information generator is configured to identify the corneal apex as the feature point, calculate a gradient of an anterior surface of a cornea at the corneal apex, and perform generation of the tilt information based on the gradient.

In the ophthalmic apparatus according to some aspect examples, the OCT imager is configured to apply OCT scanning to a region that includes at least part of the anterior surface of the iris of the subject's eye and construct the image, and the tilt information generator is configured to identify at least two points on the anterior surface of the iris as the feature point and perform generation of the tilt information based on the at least two points.

Some aspect examples are a method of controlling an ophthalmic apparatus that includes a fixation target presenting unit configured to present a fixation target to a subject, a scanner configured to apply optical coherence tomography (OCT) scanning to an anterior eye segment of a subject's eye, and at least one processor, the method being configured to cause the at least one processor to perform a step of constructing an image based on data collected by the scanner, a step of generating tilt information that represents a tilt state of the anterior eye segment depicted in the image, and a step of controlling the fixation target presenting unit based on the tilt information.

Some aspect examples are a method of controlling an ophthalmic apparatus that includes a fixation target presenting unit configured to present a fixation target to a subject, a scanner configured to apply optical coherence tomography (OCT) scanning to an anterior eye segment of the subject's eye, an operation device configured to generate a signal upon receipt of an operation, and at least one processor, the method being configured to cause the at least one processor to perform a step of constructing an image based on data collected by the scanner, a step of generating tilt information that represents a tilt state of the anterior eye segment depicted in the image, a step of displaying information based on the tilt information on a display device, and a step of controlling the fixation target presenting unit based on the signal from the operation device.

Some aspect examples are a program configured to cause a computer to execute the method according to any aspect example.

Some aspect examples are a computer-readable non-transitory recording medium in which the program according to any aspect example is recorded.

The aspect examples are capable of improving OCT anterior eye segment analysis.

BRIEF DESCRIPTION OF THE SEVERAL
VIEWS OF THE DRAWING

DETAILED DESCRIPTION

Figure 1:
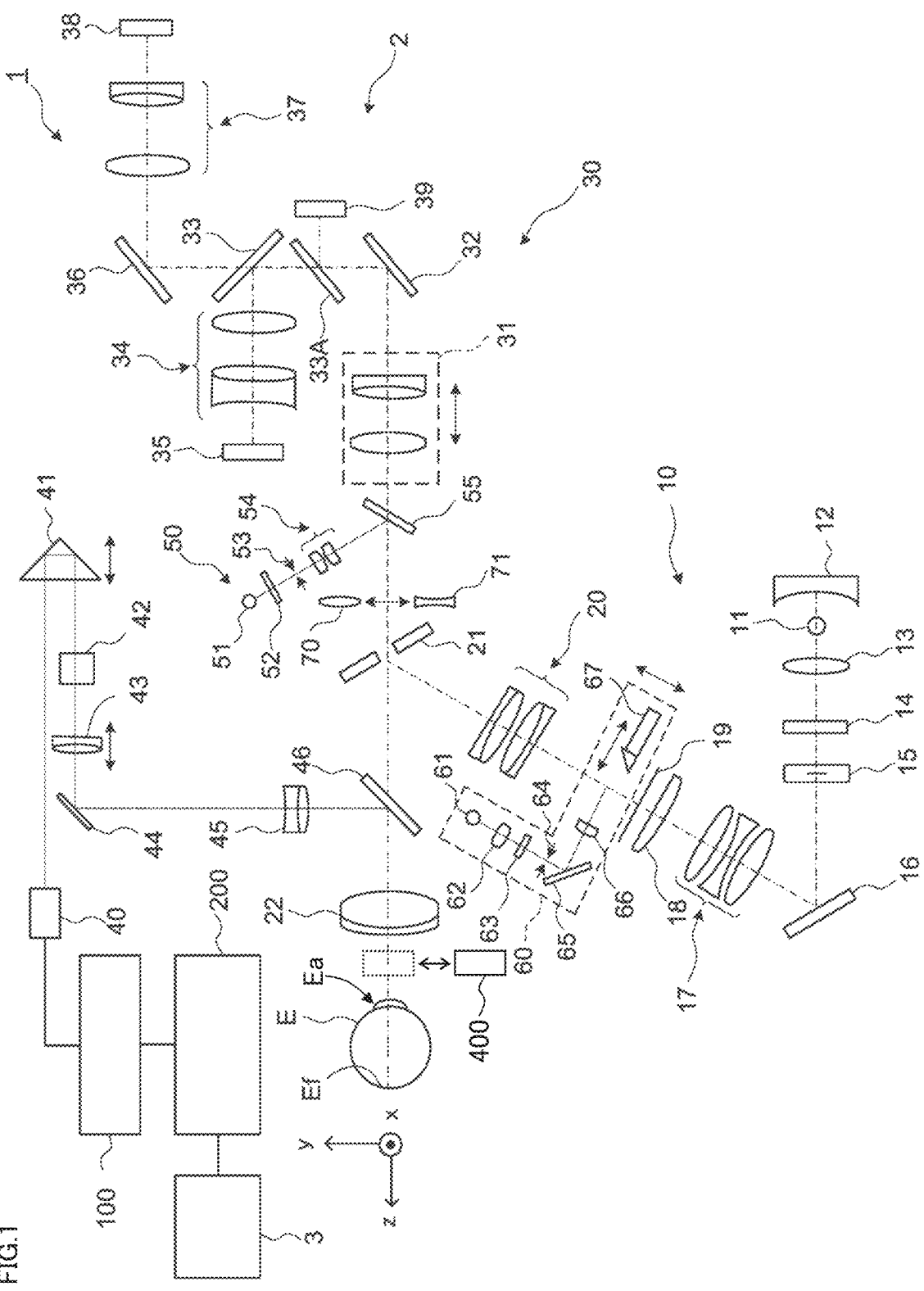
FIG. 1 is a diagram illustrating an example of a configuration of an ophthalmic apparatus according to an aspect example.

The present disclosure describes several aspect examples of embodiments of an ophthalmic apparatus, a method of controlling the same, a program, and a recording medium with referring to the drawings. Any matters and items disclosed in the documents cited in the present disclosure and any matters and items related to any other known technologies and techniques may be combined with the aspect examples described in the present disclosure. Note that "image data" and an "image" formed based on this image data are not distinguished in the present disclosure unless otherwise mentioned. Similarly, a "site (part, tissue, etc.)" of a subject's eye and an "image" of this site are not distinguished in the present disclosure unless otherwise mentioned.

An ophthalmic apparatus according to some aspect examples is configured to be capable of measuring and imaging the fundus of a living eye by applying Fourier domain OCT techniques (e.g., swept source OCT techniques). The types of OCT techniques applicable to aspect examples are not limited to swept source OCT techniques, and spectral domain OCT techniques or time domain OCT techniques may be applied to some aspect examples.

An ophthalmic apparatus according to some aspect examples may be configured to be capable of executing processing of an image acquired by a modality other than OCT. For example, some aspect examples may be configured to be capable of executing processing of an image acquired by any of a fundus camera (retinal camera), a laser scanning ophthalmoscope (SLO), a slit lamp microscope, and an ophthalmic surgical microscope. An ophthalmic apparatus according to some aspect examples may include one or more of a fundus camera, an SLO, a slit lamp microscope, and an ophthalmic surgical microscope.

An ophthalmic apparatus according to some aspect examples is configured to acquire an image constructed based on data collected from the anterior eye segment of a living eye by applying OCT scanning, and to apply processing to this image. This image is referred to as an anterior eye segment image.

An ophthalmic apparatus according to some aspect examples include a configuration of collecting data by applying OCT scanning to the anterior eye segment of a living eye and a configuration of constructing an anterior eye segment image based on the data collected. An ophthalmic apparatus according to some aspect examples may have a function of receiving an anterior eye segment image of a living eye from outside. In some examples, an anterior eye segment image of a living eye is acquired by using an OCT apparatus and this anterior eye segment image is stored in a medical image management system such as a picture archiving and communication system (PACS). An ophthalmic apparatus according to some aspect examples is configured to access to the medical image management system and obtain an anterior eye segment image.

In addition to descriptions of such an ophthalmic apparatus, the present disclosure gives descriptions of a method of controlling an ophthalmic apparatus, descriptions of a program of causing a computer to execute such a method, and descriptions of a recording medium storing such a program.

At least one or more of the functions of the elements described in the present disclosure are implemented by using a circuit configuration (circuitry) or a processing circuit configuration (processing circuitry). The circuitry or the processing circuitry includes any of the followings, all of which are configured and/or programmed to execute at least one or more functions disclosed herein: a general purpose processor, a dedicated processor, an integrated circuit, a central processing unit (CPU), a graphics processing unit (GPU), an application specific integrated circuit (ASIC), a programmable logic device (e.g., a simple programmable logic device (SPLD), a complex programmable logic device (CPLD), or a field programmable gate array (FPGA)), an existing or conventional circuit configuration or circuitry, and any combination of these. A processor is considered to be processing circuitry or circuitry that includes a transistor and/or another circuitry. In the present disclosure, circuitry, a unit, a means, or a term similar to these is hardware that executes at least one or more functions disclosed herein, or hardware that is programmed to execute at least one or more functions disclosed herein. Hardware may be the hardware disclosed herein, or alternatively, known hardware that is programmed and/or configured to execute at least one or more functions described herein. In the case where the hardware is a processor, which may be considered as a certain type of circuitry, then circuitry, a unit, a means, or a term similar to these is a combination of hardware and software. In this case, the software is used to configure the hardware and/or the processor.

<Configuration of Ophthalmic Apparatus>

The ophthalmic apparatus 1 of an aspect example shown in FIG. 1 is a multifunction apparatus that is a combination of an OCT apparatus and a fundus camera, and has both the function of applying OCT scanning to the anterior eye segment Ea of the subject's eye E and the function of conducting photography of the anterior eye segment Ea. The ophthalmic apparatus 1 includes the fundus camera unit 2, the OCT unit 100, and the arithmetic and control unit 200. The fundus camera unit 2 is provided with an element group (e.g., optical elements, mechanisms, etc.) for acquiring a front image of a subject's eye. The OCT unit 100 includes part of an element group (e.g., optical elements, mechanisms, etc.) for conducting OCT scanning. Another part of the element group for conducting OCT scanning is provided in the fundus camera unit 2. The arithmetic and control unit 200 includes one or more processors configured and programmed to execute various processes (e.g., calculations, controls, etc.), and one or more storage devices (memories). In addition to these elements, the ophthalmic apparatus 1 may also include any elements and/or any units such as a member for supporting the face of the subject, an attachment for switching or changing sites of a subject's eye to which OCT scanning is applied. Here, examples of the member for supporting the face of the subject include a chin rest and a forehead rest.

A description is now given of some examples of the attachment for switching or changing sites of a subject's eye to which OCT scanning is applied. An example attachment includes a lens group (lens unit). The anterior eye segment OCT attachment 400 (the attachment for anterior eye segment OCT 400) includes a lens group used for switching sites of the subject's eye E to which OCT scanning is applied between the posterior eye segment (fundus Ef) and the anterior eye segment Ea. The anterior eye segment OCT attachment 400 may have the same configuration as that of an optical unit disclosed in Japanese Unexamined Patent Application Publication No. 2015-160103.

As illustrated in FIG. 1, the anterior eye segment OCT attachment 400 is inserted between the objective lens 22 and the subject's eye E. In the state in which the anterior eye segment OCT attachment 400 is placed in the optical path, the ophthalmic apparatus 1 can apply OCT scanning to the anterior eye segment Ea of the subject's eye E. On the other hand, in the state in which the anterior eye segment OCT attachment 400 is removed from the optical path, the ophthalmic apparatus 1 can apply OCT scanning to the posterior eye segment of the subject's eye E. The movement (insertion and removal) is performed by hand or by machine (manually or automatically).

An ophthalmic apparatus of some aspect examples may be configured to apply OCT scanning to a posterior eye segment in the state in which an attachment is inserted in an optical path and to apply OCT scanning to an anterior eye segment in the state in which this attachment is removed from this optical path. Sites of a subject's eye to which OCT scanning is applied switched by an attachment are not limited to the combination of anterior eye segment and posterior eye segment, and may be any combinations of ocular sites. Also, a configuration for switching sites of a subject's eye to which OCT scanning are applied, is not limited to attachments like the one described above (lens group, lens unit, optical unit), and some examples of the configuration for the site switching may include one or more lenses movable along an optical path.

<Fundus Camera Unit 2>

The fundus camera unit 2 includes elements (e.g., optical systems, mechanisms, etc.) for acquiring digital images (digital photographs, digital pictures) by conducting photography of the subject's eye E (e.g., the anterior eye segment Ea, fundus Ef, etc.). The digital images of the subject's eye E acquired are front images (en face images) such as observation images and photographed images. An observation image is obtained, for example, by capturing a moving image using near-infrared light, and may be used for alignment, focusing, tracking, and other operations. A photographed image is a still image obtained using visible flash light or infrared flash light, for example, and may be used for diagnosis, analysis, and so forth.

The fundus camera unit 2 includes the illumination optical system 10 and the photography optical system 30. The illumination optical system 10 projects illumination light onto the subject's eye E. The photography optical system 30 detects return light of the illumination light from the subject's eye E. Measurement light entered from the OCT unit 100 is directed to the subject's eye E through an optical path in the fundus camera unit 2, and return light of this measurement light from the subject's eye E is directed to the OCT unit 100 through the same optical path.

Light emitted by the observation light source 11 of the illumination optical system (referred to as observation illumination light) is reflected by the concave mirror 12, passes through the condenser lens 13, and becomes near-infrared light after passing through the visible cut filter 14. Further, the observation illumination light is once converged at a location near the photographing light source 15, reflected by the mirror 16, and passes through the relay lens system 17, the relay lens 18, the diaphragm 19, and the relay lens system 20. Then, the observation illumination light is reflected on the peripheral part (i.e., the area surrounding the aperture part) of the aperture mirror 21, penetrates the dichroic mirror 46, and refracted by the objective lens 22, thereby illuminating the subject's eye E. Return light of the observation illumination light from the subject's eye E is refracted by the objective lens 22, penetrates the dichroic mirror 46, passes through the aperture part formed in the center area of the aperture mirror 21, passes through the dichroic mirror 55, travels through the photography focusing lens 31, and is reflected by the mirror 32. Furthermore, the return light of the observation illumination light passes through the half mirror 33A, is reflected by the dichroic mirror 33, and forms an image on the light receiving surface of the image sensor 35 by the imaging lens 34. The image sensor 35 detects the return light at a predetermined frame rate. The photography optical system 30 is adjusted to be focused on the fundus Ef or the anterior eye segment Ea.

Light emitted by the photographing light source 15 (referred to as photographing illumination light) passes through the same route as the route of the observation illumination light and is projected onto the fundus Ef. Return light of the photographing illumination light from the subject's eye E passes through the same route as the route of the return light of the observation illumination light to the dichroic mirror 33, passes through the dichroic mirror 33, is reflected by the mirror 36, and forms an image on the light receiving surface of the image sensor 38 by the imaging lens 37.

The liquid crystal display (LCD) 39 displays a fixation target (fixation target image). Part of a light beam output from the LCD 39 is reflected by the half mirror 33A and the mirror 32, travels through the photography focusing lens 31 and the dichroic mirror 55, and passes through the aperture part of the aperture mirror 21. The light beam having passed through the aperture part of the aperture mirror 21 penetrates the dichroic mirror 46, and is refracted by the objective lens 22, thereby being projected onto the fundus Ef.

Varying the display position of the fixation target image on the LCD 39 can be used to change fixation position (also referred to as fixation direction) of the subject's eye E by the fixation target. That is, the line of sight of the subject's eye E can be guided in a desired direction by changing the fixation position. The ophthalmic apparatus 1 may be provided with a graphical user interface (GUI) used for designation of a desired fixation position.

Configurations for presenting, to the subject's eye E, a fixation target in such a manner that a fixation position can be changed, are not limited to a display device such as LCD. For example, a fixation matrix may be used, in place of such a display device, that includes a plurality of light emitting elements (e.g., light emitting diodes or the like) arranged in a matrix pattern (array pattern). In this example case, a fixation position can be changed by selecting and turning on a light emitting element. In another example case, a fixation position can be changed by means of one or more movable light emitting elements.

The alignment optical system 50 generates an alignment indicator used for alignment of the optical system with respect to the subject's eye E. Alignment light emitted by the light emitting diode (LED) 51 travels through the diaphragm 52, the diaphragm 53, and the relay lens 54, is reflected by the dichroic mirror 55, passes through the aperture part of the aperture mirror 21, penetrates the dichroic mirror 46, and is projected onto the subject's eye E via the objective lens 22. Return light of the alignment light from the subject's eye E passes through the same route as the route of the return light of the observation illumination light and is guided to the image sensor 35. An image detected by the image sensor 35 (alignment indicator image) is used for performing manual alignment and/or automatic alignment.

As in existing or conventional techniques, the alignment indicator image of the present example includes two bright spot images whose positions change depending on alignment states (alignment conditions). When the relative position between the subject's eye E and the optical system changes in the xy direction, the two bright spot images are shifted together in the xy direction. When the relative position between the subject's eye E and the optical system changes in the z direction, the relative position (the distance) between the two bright spot images changes. In the state in which the distance between the subject's eye E and the optical system in the z direction matches with a working distance set in advance, the two bright spot images overlap each other. In the state in which the position of the subject's eye E matches with the position of the optical system in the xy direction, the two bright spot images are located within or near an alignment target set in advance. In the state in which the distance between the subject's eye E and the optical system in the z direction matches with the working distance as well as the position of the subject's eye E matches with the position of the optical system in the xy direction, the two bright spot images overlap each other and are located within the alignment target.

When conducting automatic alignment, the data processor 230 detects the positions of the two bright spot images, and the main controller 211 controls the movement mechanism 150 (described later) on the basis of the positional relationship between the two bright spot images and the alignment target. When conducting manual alignment, the main controller 211 displays the two bright spot images together with an observation image of the subject's eye E on the display 241, and the user manipulates the operation device 242 to operate the movement mechanism 150 while monitoring the two bright spot images displayed.

The methods and techniques of alignment are not limited to those described above. An ophthalmic apparatus according to some aspect examples may include an alignment unit configured to perform the following processes (see, for example, Japanese Unexamined Patent Application Publication No. 2013-248376): a process of acquiring two or more photographed images of an anterior eye segment of a subject's eye by substantially simultaneously conducting two or more operations of anterior eye segment photography of the anterior eye segment from two or more different directions; a process of calculating a three dimensional position of the subject's eye by analyzing the two or more photographed images; and a process of moving an optical system based on the three dimensional position calculated.

The focusing optical system 60 generates a split indicator used for focus adjustment (focusing, focusing operation) with respect to the subject's eye E. The focusing optical system 60 is moved along the optical path of the illumination optical system 10 in conjunction with movement of the photography focusing lens 31 along the optical path of the photography optical system 30. The optical path of the illumination optical system 10 is referred to as the illumination optical path, and the optical path of the photography optical system 30 is referred to as the photography optical path. The reflection rod 67 is inserted into and removed from the illumination optical path. The reflective surface of the reflection rod 67 is inserted into the illumination optical path and placed in an oblique orientation before performing focus adjustment. Focus light emitted by the LED 61 passes through the relay lens 62, is split into two light beams by the split indicator plate 63, and passes through the two-hole diaphragm 64. The focus light, then, is reflected by the mirror 65, is converged on the reflective surface of the reflection rod 67 by the condenser lens 66, and is reflected by the reflective surface. Further, the focus light travels through the relay lens 20, is reflected by the aperture mirror 21, and penetrates the dichroic mirror 46, thereby being projected onto the subject's eye E via the objective lens 22. Return light of the focus light from the subject's eye E passes through the same route as the route of the return light of the alignment light and is guided to the image sensor 35. An image detected by the image sensor 35 (split indicator image) is used for performing manual focusing and/or automatic focusing.

The diopter correction lenses 70 and 71 are selectively inserted into the photography optical path between the aperture mirror 21 and the dichroic mirror 55. The diopter correction lens 70 is a positive lens (convex lens) for correcting high hyperopia. The diopter correction lens 71 is a negative lens (concave lens) for correcting high myopia.

The dichroic mirror 46 couples the optical path for digital photography and the optical path for OCT scanning. The optical path for digital photography includes the illumination optical path and the photography optical path. The optical path for OCT scanning is referred to as a sample arm. The dichroic mirror 46 reflects light of wavelength bands used for OCT scanning while transmitting light for digital photography. Listed from the OCT unit 100 side, the sample arm includes the collimator lens unit 40, the retroreflector 41, the dispersion compensation member 42, the OCT focusing lens 43, the optical scanner 44, and the relay lens 45.

The retroreflector 41 is movable in the directions indicated by the arrow in FIG. 1. These directions are the direction in which the measurement light LS is incident onto the subject's eye E and the direction in which return light of the measurement light LS from the subject's eye E travels. With this movement of the retroreflector 41, the length of the sample arm is changed. This change in the sample arm length may be used for operations such as optical path length correction on the basis of eye axial length, optical path length correction on the basis of corneal shape and/or eye fundus shape, and adjustment or regulation of interference conditions or states.

The dispersion compensation member 42, together with the dispersion compensation member 113 (described later) arranged in the reference arm, acts to equalize the dispersion characteristics of the measurement light LS and the dispersion characteristics of the reference light LR with each other.

The OCT focusing lens 43 is movable in the directions indicated by the arrow in FIG. 1 (that is, movable along the optical axis of the sample arm) in order to perform focus adjustment of the sample arm. With this movement of the OCT focusing lens 43, the focus conditions or the focus states (focal position, focal length) of the sample arm is changed. The ophthalmic apparatus 1 may be configured to be capable of executing interlocking control between the movement of the photography focusing lens 31, the movement of the focusing optical system 60, and the movement of the OCT focusing lens 43.

The optical scanner 44 is placed substantially at a position optically conjugate with the pupil of the subject's eye E. The optical scanner 44 deflects the measurement light LS guided by the sample arm. The optical scanner 44 of some examples may be a deflection system capable of two dimensional scanning that includes a deflector for performing scanning in the x direction and a deflector for performing scanning in the y direction (x-scanner and y-scanner). The optical scanner 44 of some examples may be a galvanometer scanner including two galvanometer mirrors. In some typical examples, one of the two deflectors is arranged at a position optically conjugate with the pupil of the subject's eye E, or the position optically conjugate with the pupil is arranged at a position between the two deflectors. Such arrangement makes it capable of OCT scanning of the fundus Ef in which the measurement light LS is deflected around a pivot located at a position in (or near) the pupil of the subject's eye E, which makes it possible to apply OCT scanning to a wide (broad) area of the fundus Ef.

In the present aspect, the optical scanner 44 is placed at a position substantially optically conjugate with the pupil of the subject's eye E as described above when the anterior eye segment OCT attachment 400 is not placed in the sample arm. On the other hand, the optical scanner 44 is placed at a position substantially optically conjugate with a position between the anterior eye segment Ea and the anterior eye segment OCT attachment 400 when the anterior eye segment OCT attachment 400 is placed in the optical path. More specifically, in the case in which the anterior eye segment OCT attachment 400 is removed from the sample arm, for example, one of the x-scanner and the y-scanner is placed at a position substantially optically conjugate with the pupil, or a position between the x-scanner and the y-scanner is placed at a position substantially optically conjugate with the pupil. Further, in the case in which the anterior eye segment OCT attachment 400 is inserted in the sample arm, for example, one of the x-scanner and the y-scanner is placed at a position substantially optically conjugate with the anterior eye segment Ea, or a position between the x-scanner and the y-scanner is placed at a position substantially optically conjugate with a position between the anterior eye segment Ea and the anterior eye segment OCT attachment 400.

<OCT Unit 100>

Figure 2:
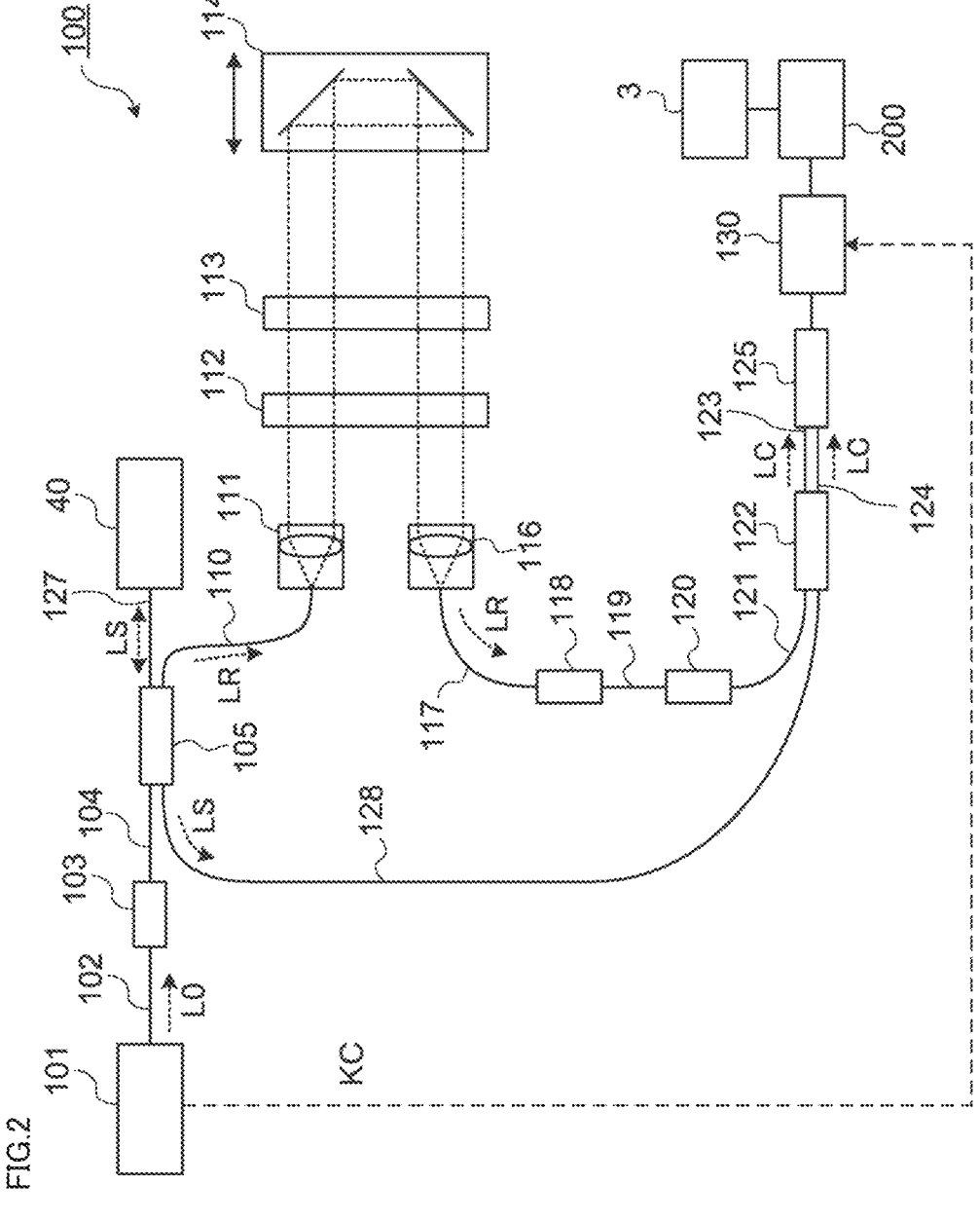
FIG. 2 is a diagram illustrating an example of a configuration of an ophthalmic apparatus according to an aspect example.

As illustrated in FIG. 2, the OCT unit 100 is provided with an optical system and mechanisms for performing swept source OCT. This optical system includes an interference optical system. This interference optical system is configured to split light emitted by a wavelength tunable light source (wavelength sweeping light source) into measurement light and reference light, to generate interference light by superposing return light of the measurement light from the subject's eye E on the reference light that has been guided by a reference optical path (reference arm), and to detect this interference light. A result of this interference light detection (detection signal) obtained by the interference optical system, is a signal representing a spectrum of the interference light. This detection signal is sent to the arithmetic and control unit 200 (image constructing unit 220).

The light source unit 101 of some examples includes a near-infrared wavelength tunable laser configured to vary the wavelengths of emitted light at high speed. The light LO output from the light source unit 101 is guided to the polarization controller 103 through the optical fiber 102. The polarization controller 103 is configured to perform regulation (adjustment) of the polarization condition (polarization state) of the light LO. Further, the light LO is guided to the fiber coupler 105 through the optical fiber 104. The fiber coupler 105 is configured to split the light LO into the measurement light LS and the reference light LR. The optical path of the measurement light LS is referred to as the sample arm or the like, and the optical path of the reference light LR is referred to as the reference arm or the like.

The reference light LR is guided through the optical fiber 110 to the collimator 111, is converted into a parallel light beam by the collimator 111, travels through the optical path length correction member 112 and the dispersion compensation member 113, and is guided to the retroreflector 114. The optical path length correction member 112 is an optical element for equalizing the optical path length of the reference light LR and the optical path length of the measurement light LS with each other. The dispersion compensation member 113 is an optical element for equalizing the dispersion characteristics of the reference light LR and the dispersion characteristics of the measurement light LS with each other, together with the dispersion compensation member 42 disposed in the sample arm. The retroreflector 114 is movable along the optical path of the reference light LR that is incident onto the retroreflector 114. With this, the length of the reference arm is changed. This change in the reference arm length may be used for operations such as optical path length correction on the basis of eye axial length, optical path length correction on the basis of corneal shape and/or eye fundus shape, and adjustment or regulation of interference conditions or states.

The reference light LR that has passed through the retroreflector 114 travels through the dispersion compensation member 113 and the optical path length correction member 112, is converted from a parallel light beam to a convergent light beam by the collimator 116, and is incident onto the optical fiber 117. The reference light LR that has entered the optical fiber 117 is guided to the polarization controller 118, and the polarization state of the reference light LR is regulated by the polarization controller 118. The polarization controller 118 is an optical device for interference condition regulation (interference state adjustment, interference state regulation, interference state adjustment). The polarization controller 118 is used for optimizing the strength of interference (coherence) between the measurement light LS and the reference light LR, for example. The reference light LR output from the polarization controller 118 is guided to the attenuator 120 through the optical fiber 119, and the amount of light of the reference light LR is regulated by the attenuator 120. Subsequently, the reference light LR is guided to the fiber coupler 122 through the optical fiber 121.

Meanwhile, the measurement light LS generated by the fiber coupler 105 is guided through the optical fiber 127 to the collimator lens unit 40 and is converted to a parallel light beam by the collimator lens unit 40. The measurement light LS output from the collimator lens unit 40 passes through the retroreflector 41, the dispersion compensation member 42, the OCT focusing lens 43, the optical scanner 44, and the relay lens 45, is reflected by the dichroic mirror 46, and is refracted by the objective lens 22, thereby being projected onto the subject's eye E. When the anterior eye segment OCT attachment 400 is placed in the sample arm, the measurement light LS reflected by the dichroic mirror 46 is projected onto the subject's eye E (anterior eye segment Ea) via the objective lens 22 and the anterior eye segment OCT attachment 400. The measurement light LS is reflected and scattered at various depth positions of the subject's eye E. Return light of the measurement light LS from the subject's eye E travels along the same route as the outward way in the opposite direction to the fiber coupler 105, and then reaches the fiber coupler 122 through the optical fiber 128.

The fiber coupler 122 superposes the measurement light LS reached here through the optical fiber 128 with the reference light LR reached here through the optical fiber 121 to generate interference light. The fiber coupler 122 splits the interference light generated by the fiber coupler 122 at a predetermined splitting ratio (e.g., 1 to 1) to generate a pair of interference light LC. The pair of interference light LC is guided to the detector 125 through the optical fibers 123 and 124, respectively.

The detector 125 of some examples includes a balanced photo diode. This balanced photodiode includes a pair of photodetectors that detects the pair of the interference light LC respectively. The balanced photodiode outputs a difference signal between a pair of detection signals corresponding to the pair of the interference light LC respectively obtained by the pair of photodetectors. The detector 125 sends this output (difference signal, detection signal) to the data acquisition system (DAS) 130.

The clock KC is supplied from the light source unit 101 to the data acquisition system 130. The clock KC is generated in the light source unit 101 in synchronization with the output timings of individual wavelengths varied over a predetermined wavelength range by the wavelength tunable light source. The light source unit 101 of some examples is configured to split the light LO of the individual output wavelengths to generate two pieces of split light, to apply an optical delay to one of the two pieces of split light, to superpose the resulting two pieces of split light with one another, to detect the resulting superposed light, and to generate the clock KC based on the detection result of the superposed light. Based on the clock KC, the data acquisition system 130 performs sampling of the detection signal input from the detector 125. The data acquisition system 130 sends the result of this sampling to the arithmetic and control unit 200.

The present aspect example is provided with both an element for changing the sample arm length (e.g., the retroreflector 41) and an element for changing the reference arm length (e.g., the retroreflector 114 or a reference mirror). However, some other aspect examples may be provided with only either one of these two elements. An element for changing the difference between the sample arm length and the reference arm length (i.e., an element for changing the optical path length difference) is not limited to these examples described herein, and may be freely selected element such as any optical member and/or any mechanism.

As described above, swept source OCT is a technique including the following processes: a process of splitting light emitted by a wavelength tunable light source into measurement light and reference light; a process of generating interference light by superposing return light of the measurement light from a sample and the reference light; a process of detecting the interference light by a photodetector; and a process of constructing an image of the sample by applying signal processing including a Fourier transform to detection data collected corresponding to wavelength sweeping (change in emitted wavelengths) and scanning with the measurement light.

Spectral domain OCT, an alternative to swept source OCT, is a technique including the following processes: a process of splitting light emitted by a low coherence light source (broad band light source, wide band light source) into measurement light and reference light; a process of generating interference light by superposing return light of the measurement light from a sample and the reference light; a process of detecting a spectral distribution (spectral components) of the interference light by a spectrometer; and a process of constructing an image of the sample by applying signal processing including a Fourier transform to the spectral distribution detected.

In short, swept source OCT can be said to be an OCT technique of acquiring a spectral distribution of interference light in a time-divisional manner while spectral domain OCT can be said to be an OCT technique of acquiring a spectral distribution of interference light in a space-divisional manner.

<Control System and Processing System>

Figure 3:
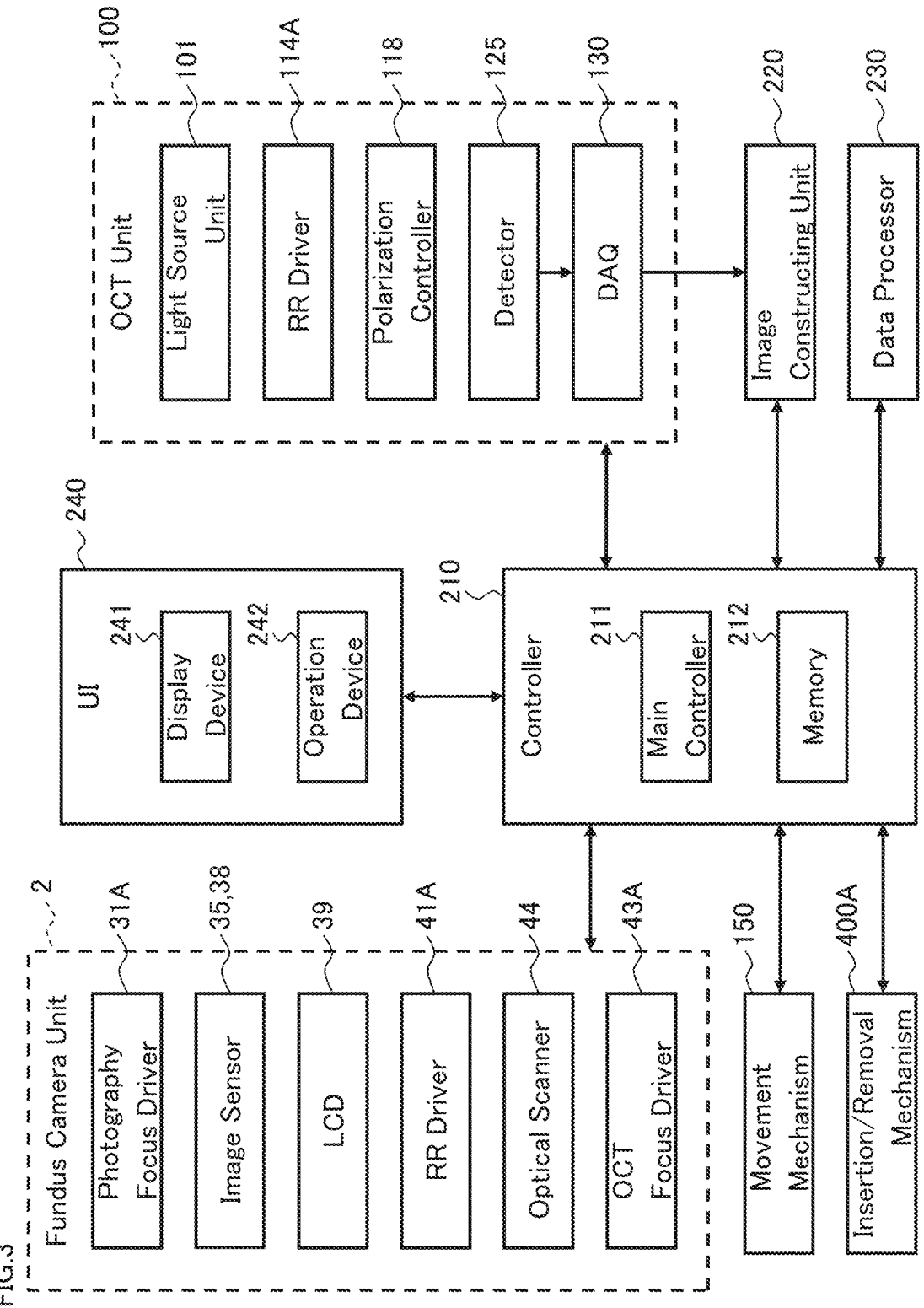
FIG. 3 is a diagram illustrating an example of a configuration of an ophthalmic apparatus according to an aspect example.

FIG. 3 illustrates an example of the configuration of the control system and the processing system of the ophthalmic apparatus 1. The arithmetic and control unit 200 of some examples may include the controller 210, the image constructing unit 220, and the data processor 230. The ophthalmic apparatus 1 may further include a communication device for performing data communication with external apparatuses. The ophthalmic apparatus 1 may further include a drive device (reader and/or writer) for reading out data from recording media and writing data into recording media.

<Controller 210>

The controller 210 is configured to perform various kinds of controls. The controller 210 includes the main controller 211 and the memory 212. The main controller 211 includes one or more processors and executes a control of each element of the ophthalmic apparatus 1 (including the elements shown in FIG. 1 to FIG. 4). The main controller 211 performs a control of the LCD 39 in order to conduct a control related to the fixation target. The main controller 211 is implemented by cooperation between hardware including the one or more processors and control software.

The photography focus driver 31A is configured to move the photography focusing lens 31 disposed in the photography optical path and the focusing optical system 60 disposed in the illumination optical path under control of the main controller 211. The retroreflector driver (RR driver) 41A is configured to move the retroreflector 41 disposed in the sample arm under control of the main controller 211. The OCT focus driver 43A is configured to move the OCT focusing lens 43 disposed in the sample arm under control of the main controller 211. The retroreflector driver (RR driver) 114A is configured to move the retroreflector 114 disposed in the reference arm under control of the main controller 211. Each of the above drivers includes an actuator, such as a pulse motor, that operates under control of the main controller 211. The optical scanner 44 also operates under control of the main controller 211.

The movement mechanism 150 of some examples is configured to move the fundus camera unit 2 in a three dimensional manner. The movement mechanism 150 of some typical examples includes the following elements: an x stage that is movable in the ±x directions (left and right directions); an x movement mechanism configured to move the x stage; a y stage that is movable in the ±y directions (upward and downward directions); a y movement mechanism configured to move the y stage; a z stage that is movable in the ±z directions (front and back directions, depth direction); and a z movement mechanism configured to move the z stage. Each of these movement mechanisms includes an actuator, such as a pulse motor, that operates under control of the main controller 211.

The insertion and removal mechanism 400A is configured to perform an operation of inserting the anterior eye segment OCT attachment 400 into the OCT optical path (sample arm), and an operation of removing the anterior eye segment OCT attachment 400 from the sample arm. The insertion and removal mechanism 400A includes an actuator, such as a solenoid actuator, that operates under control of the main controller 211.

The memory 212 retains various kinds of data. Examples of data stored in the memory 212 include OCT images, digital images (anterior eye segment images, fundus images), subject's eye information, and analysis data. The subject's eye information includes subject information such as a patient identifier (patient ID) and a patient's name, identification information for right and left eyes, and electronic medical record information.

<Image Constructing Unit 220>

The image constructing unit 220 includes one or more processors and is configured to construct OCT image data of the subject's eye E based on signals (sampling data) input from the data acquisition system 130. The OCT image data constructed by the image constructing unit 220 is one or more pieces of A-scan image data, and typically is B-scan image data (two dimensional cross sectional image data, two dimensional tomographic image data) consisting of a plurality of pieces of A-scan image data.

The process of constructing OCT image data includes noise elimination (noise reduction), filtering, fast Fourier transform (FFT), and other processes, as in existing or conventional Fourier domain OCT techniques. In the cases in which other types of OCT techniques are employed, the image constructing unit 220 executes known processing in accordance with an OCT technique employed.

The image constructing unit 220 may be configured to construct three dimensional data of the subject's eye E based on signals input from the data acquisition system 130. This three dimensional data is three dimensional image data representing a three dimensional region (referred to as a volume) of the subject's eye E. This three dimensional image data is image data in which the positions of pixels are defined using a three dimensional coordinate system. Examples of such three dimensional image data include stack data and volume data.

Stack data is image data formed by arranging (disposing), in a three dimensional manner, a plurality of cross sectional images acquired along a plurality of scan lines, on the basis of the positional relationship between these scan lines. In other words, stack data is image data constructed by representing multiple cross sectional images, which are originally defined in individually different two dimensional coordinate systems, with a single three dimensional coordinate system, that is, by embedding the multiple cross sectional images into a single three dimensional space. In further other words, stack data is image data formed by arranging, in a three dimensional manner, a plurality of A-scan image data acquired respectively for a plurality of scan points arranged in a two dimensional manner (that is, for a scan point array), on the basis of the positional relationship between these scan points.

Volume data is image data whose elements (picture elements) are voxels arranged in a three dimensional manner. Volume data is also referred to as voxel data. volume data is constructed by applying processing such as interpolation and voxelization to stack data.

The image constructing unit 220 constructs an image for display, by applying rendering to three dimensional image data. Examples of applicable rendering techniques include volume rendering, surface rendering, maximum intensity projection (MIP), minimum intensity projection (MinIP), and multi planar reconstruction (MPR).

The image constructing unit 220 may be configured to construct an OCT front image (OCT en face image) based on three dimensional image data. The image constructing unit 220 of some examples may be configured to construct projection data of three dimensional image data by applying, to the three dimensional image data, projection processing in the z direction (A-line direction, depth direction). Similarly, the image constructing unit 220 may be configured to construct projection data from partial data of three dimensional image data such as a slab of three dimensional image.

In some typical examples, partial data of three dimensional image data, such as a slab, may be obtained by using segmentation processing. Segmentation, or image segmentation, is image processing of partitioning an image to identify a partial region. Segmentation of some typical examples is performed to identify an image region corresponding to a predetermined tissue of the subject's eye E. Segmentation of some examples may include any known image processing technique, and may include, for example, image processing such as edge detection, and/or, a segmentation technique by means of machine learning (e.g., deep learning). Segmentation of the present aspect example is executed, for example, by the image constructing unit 220 or the data processor 230.

The ophthalmic apparatus 1 may be capable of performing OCT motion contrast imaging. OCT motion contrast imaging is a technique of imaging motion of fluid (liquid) etc. in an eye (see, for example, Japanese Unexamined Patent Application Publication (Translation of PCT Application) No. 2015-515894).

The image constructing unit 220 is implemented by cooperation between hardware including one or more processors and image data constructing software.

<Data Processor 230>

The data processor 230 includes one or more processors and is configured to perform various kinds of data processing on an image of the subject's eye E. The data processor 230 of some examples is implemented by cooperation between hardware including the one or more processors and data processing software.

The data processor 230 may be configured to perform position matching (registration) between two images acquired for the subject's eye E. The data processor 230 of some examples may be configured to perform registration between three dimensional image data acquired using OCT scanning and a front image (en face image) acquired by the fundus camera unit 2. The data processor 230 of some examples may be configured to perform registration between two OCT images acquired using OCT scanning. The data processor 230 of some examples may be configured to perform registration between two front images acquired by the fundus camera unit 2. The data processor 230 of some examples may be configured to apply registration to any of resulting data of analysis of one or more OCT images, resulting data of analysis of one or more front images, and other analysis results. Registration may be performed using freely selected known techniques. Registration of some examples may include feature point extraction and affine transformation.

<User Interface 240>

The user interface 240 includes the display device 241 and the operation device 242. The display device 241 includes the display device 3. The operation device 242 includes various operation devices and various input devices. The user interface 240 may include a device that has both a display function and an operation function, such as a touch panel. Some embodiment may not include at least part of the user interface 240. For example, a display device may be an external device or a peripheral device that is connected to the ophthalmic apparatus 1.

<Details of Control System and Processing System>

Figure 4:
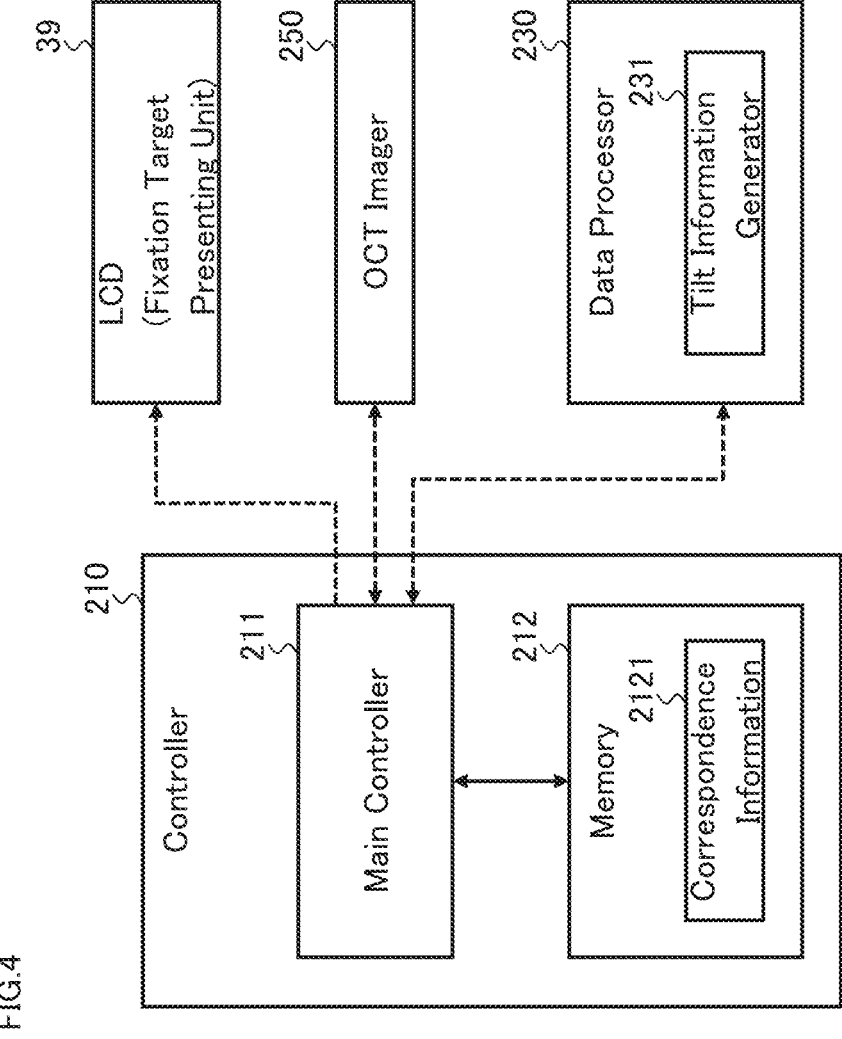
FIG. 4 is a diagram illustrating an example of a configuration of an ophthalmic apparatus according to an aspect example.

FIG. 4 shows an example of details of the configuration of the control system and the configuration of the processing system of the ophthalmic apparatus 1. In FIG. 4, elements related to characteristics and features of controls and processing of the ophthalmic apparatus 1 are selectively shown.

<LCD 39>

The LCD 39 is configured to present the fixation target to the subject's eye E. The LCD 39 is an example of a fixation target presenting unit. A fixation target presenting unit of another aspect performs presentation of a fixation target to a subject's eye (an eye to which OCT scanning is applied) by means of a configuration other than a display device such as an LCD. A fixation target presenting unit of still another aspect presents a fixation target to the fellow eye of an eye to be examined. An example of such a fixation target presenting unit is an external fixation light source.

<OCT Imager 250>

The OCT imager 250 is configured to apply OCT scanning to the anterior eye segment Ea to construct an image. The OCT imager 250 includes an element group for applying OCT scanning to the anterior eye segment Ea and an element (element group) for constructing an image from data collected by the OCT scanning. In the present aspect example, the OCT imager 250 includes the element group forming the sample arm in the fundus camera unit 2, the OCT unit 100, and the image constructing unit 220.

<Tilt Information Generator 231>

The data processor 230 of the present aspect example includes the tilt information generator 231. The tilt information generator 231 is configured to generate tilt information that represents a tilt state of the anterior eye segment Ea depicted in an image constructed by the OCT imager 250.

Some examples of the tilt information may include information that represents an orientation of the anterior eye segment Ea. This orientation information may include, for example, a value of an angle. This angle may be, for example, a tilt angle with respect to a predetermined direction in the coordinate system with which an image is defined. The predetermined direction is referred to as a reference direction. This coordinate system may be, for example, a three dimensional coordinate system (e.g., xyz coordinate system) or a coordinate system in which a subspace of the space spanned by a three dimensional coordinate system. This subspace may be a three dimensional space, a two dimensional space, or a one dimensional space.

In a typical example, the reference direction is the z direction or a direction orthogonal to the z direction (in other words, a direction defined in the xy plane), and tilt information includes a tilt angle with respect to this reference direction. The tilt angle with respect to the reference direction is defined, for example, as an angle value where the angle value for the reference direction is set to zero degrees or zero radians. Further, the tilt angle with respect to the reference direction may be information that includes both magnitude and direction (positive direction, negative direction), or may be information on magnitude only (absolute value).

Several examples of processing performed by the tilt information generator 231 will be described. For example, the tilt information generator 231 may be configured to perform a process of analyzing the image constructed by the OCT imager 250 to identify one or more feature points, and a process of generating tilt information based on the one or more feature points identified. Note that processing performed by the tilt information generator 231 is not limited to the processes of the present example. In some examples, the tilt information generator 231 may be configured to generate tilt information directly from an image constructed by the OCT imager 250 by means of an artificial intelligence engine that has been trained so as to generate tilt information from an image. The artificial intelligence engine of a typical example is an inference system that includes a machine-learned convolutional neural network.

The feature point may include, for example, any of the corner angle, the apex of the anterior surface of the crystalline lens, the corneal apex, and a point on the anterior surface of the iris. Note that the feature point is not limited to these. In some examples, the feature point may be any of the ciliary body (ciliary muscle), the zonule of Zinn, the vitreous body, and the fundus Ef, or a part thereof. The feature point may be an artificial object implanted in an eye, or a part thereof. Examples of such artificial objects include an intraocular lens (IOL), a minimally invasive (or micro-invasive) glaucoma surgery (MIGS) device, and so forth.

Image analysis used for identifying the feature point may include an image processing technique such as segmentation for identifying an image region corresponding to a predetermined site of the anterior eye segment Ea, or feature point detection for identifying a feature part (i.e., feature point) in a given image region. Segmentation of some examples may include any known image processing technique, and may include, for example, image processing such as edge detection, and/or, a segmentation technique by means of machine learning such as deep learning.

Several examples of the processing of generating tilt information based on the feature point will be described. The processing of generating tilt information from a single feature point in a specific image region may include, for example, a process of calculating the gradient (slope, inclination, titling, orientation) of the tangent line at this feature point or the gradient of the tangent plane (e.g., the gradient of the normal (normal line, normal vector) to the tangent plane) at this feature point, and a process of generating tilt information from the gradient calculated. The tilt information may be the value itself of the gradient or a value calculated from the gradient. Note that the above-mentioned specific image region is differentiable at least in a neighborhood of the feature point. For example, the image region of interest (including at least a neighborhood of the feature point) may find an approximate, differentiable shape or figure (e.g., line, curve, plane, surface, etc.) before calculation of a tangent line or a tangent plane. In an alternative example, a feature point may be identified after applying approximation by a differentiable shape or figure to the image region of interest.

The processing of generating tilt information from two or more feature points may include, for example a process of calculating the gradient of the straight line or the gradient of a plane passing through two or more feature points (e.g., the gradient of the normal line to the plane), and a process of generating tilt information from the gradient calculated. The tilt information may be the value itself of the gradient or a value calculated from the gradient. An image region to which the processing of the present example is applied need not be differentiable. Instead of considering a shape or figure (straight line or plane) passing through two or more feature points, an approximate shape or figure derived from two or more feature points may be considered. The approximate shape or figure is, for example, a shape or figure derived by regression analysis such as the least squares method.

The following is an example of a case in which the feature point is a corner angle. In the present example, the OCT imager 250 applies OCT scanning to a region that includes at least two points of the corner angle of the subject's eye E. Here, the "at least two points of the corner angle" may be a freely selected or determined plurality of points. The at least two points of the corner angle of some typical examples include a pair of opposing points on the corner angle which is distributed in an approximately circular shape.

The OCT scanning of the present example may be, for example, of any mode selected from among a B-scan, a three dimensional scan, and a radial scan. The B-scan of the present example may be, for example, the ATA scan mentioned above. A region to which the three dimensional scan of the present example is applied may be, for example, a volume whose center in the xy direction is placed at the corneal apex or the center of the pupil, or at a point near the corneal apex or the center of the pupil. The radial scan (which may be a cross scan) of the present example may include, for example, a plurality of B-scans that have individually different orientations and intersect at the corneal apex or the center of the pupil, or at a point near the corneal apex or the center of the pupil. The OCT imager 250 in the present example then constructs an image from data collected by the OCT scanning of the present example.

To begin with, the tilt information generator 231 of the present example analyzes the image constructed by the OCT imager 250 to identify the at least two points of the corner angle mentioned above as feature points. For example, the tilt information generator 231 applies segmentation to the image constructed by the OCT imager 250 to identify an image region corresponding to the cornea (corneal image) and an image region corresponding to the iris (iris image). For example, the corneal image is an image region corresponding to the posterior surface of the cornea (corneal posterior surface image), and the iris image is an image region corresponding to the anterior surface of the iris (iris anterior surface image). The tilt information generator 231 may identify the point where the corneal image (e.g., the corneal posterior surface image) and the iris image (e.g., the iris anterior surface image) intersect each other, and then determine the point of intersection as a corner angle.

Next, the tilt information generator 231 of the present example performs generation of tilt information based on the at least two points of the corner angle identified as feature points. The first to third examples of this tilt information generation will be described below. Methods of the tilt information generation are not limited to these examples.

In the first example, the tilt information generator 231 calculates the gradient of the straight line connecting two of the points of the corner angle identified as feature points, and then defines the value of the gradient or a value calculated from the gradient as tilt information (tilt angle).

In the second example, in the case where a radial scan or a three dimensional scan is employed, the tilt information generator 231 determines a plurality of pairs of opposing points, then calculates the gradient of the straight line connecting each pair of opposing points determined, and then generate tilt information (by using statistical calculation) from the plurality of gradients thus calculated. As a specific example, the tilt information generator 231 identifies the maximum value among the values of the plurality of gradients calculated, and then defines the maximum value or a value calculated from the maximum value as tilt information (tilt angle).

In the third example, in the case where a radial scan or a three dimensional scan is employed, the tilt information generator 231 identifies three or more feature points, then calculates the gradient of a plane defined from these feature points (e.g., the gradient of the normal line to the plane), and then defines the value of the gradient or a value calculated from the gradient as tilt information (tilt angle).

Figure 5A:
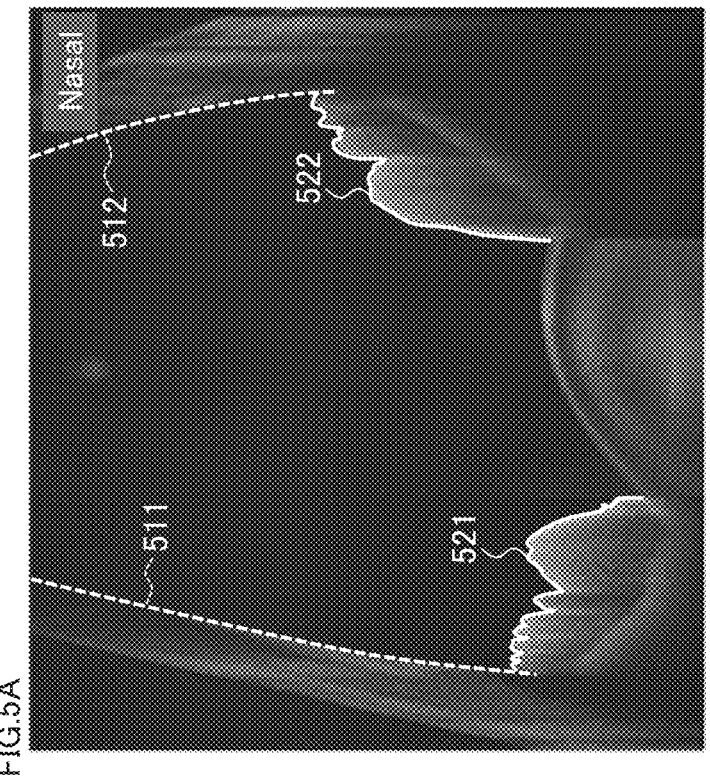
FIG. 5A is a diagram for describing an example of processing executed by an ophthalmic apparatus according to an aspect example.
Figure 5B:
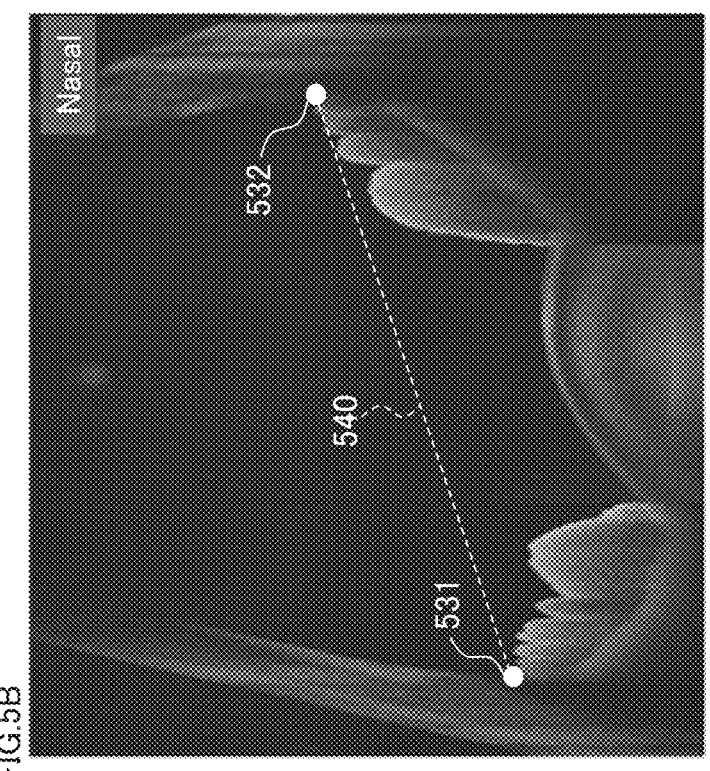
FIG. 5B is a diagram for describing an example of processing executed by an ophthalmic apparatus according to an aspect example.

A specific example in which the feature point is the corner angle is described below, referring to FIG. 5A and FIG. 5B. In the first step, the tilt information generator 231 identifies the corneal posterior surface images 511 and 512 and the iris anterior surface images 521 and 522 shown in FIG. 5A by applying segmentation to an image obtained by means of ATA scanning. The corneal posterior surface images 511 and the iris anterior surface image 521 are located on the left edge side of the image frame (near the left edge side of the image frame), and the corneal posterior surface images 512 and the iris anterior surface image 522 are located on the right edge side of the image frame (near the right edge side of the image frame). In the next step, the tilt information generator 231 identifies the position where the corneal posterior surface images 511 and the iris anterior surface image 521 intersect, and defines this intersection position as the corner angle feature point 531 (see FIG. 5B). Likewise, the tilt information generator 231 identifies the position where the corneal posterior surface images 512 and the iris anterior surface image 522 intersect, and defines this intersection position as the corner angle feature point 532 (see FIG. 5B). The corner angle feature point 531 is located on the left edge side of the image frame, and the corner angle feature point 532 is located on the right edge side of the image frame. In the final step, the tilt information generator 231 calculates the gradient of the straight line 540 that connects the corner angle feature point 531 and the corner angle feature point 532, and then defines the value of this gradient (or a value calculated from the gradient) as a tilt angle (see FIG. 5B). The tilt angle derived in this way can be used as an example of tilt information that represents a tilt state of the anterior eye segment Ea in the case where the ATA scanning of the present example is employed.

An example in which the feature point is the apex of the anterior surface of the crystalline lens is described below. In the present example, the OCT imager 250 applies OCT scanning to a region that includes the apex of the anterior surface of the crystalline lens of the subject's eye E (or, includes the vicinity of this apex). The OCT scanning of the present example may be, for example, a B-scan, a three dimensional scan, or a radial scan. The B-scan of the present example may be, for example, the ATA scan mentioned above. The region to which the three dimensional scan of the present example is applied may be, for example, a volume whose center in the xy direction is placed at the apex of the anterior surface of the crystalline lens or the vicinity thereof. The radial scan (which may be a cross scan) of the present example may include, for example, a plurality of B-scans that have individually different orientations and intersect at the apex of the anterior surface of the crystalline lens or the vicinity thereof. The OCT imager 250 of the present example then constructs an image from data collected by the OCT scanning of the present example.

The tilt information generator 231 of the present example first analyzes the image constructed by the OCT imager 250 to identify the apex of the anterior surface of the crystalline lens as a feature point. For example, the tilt information generator 231 applies segmentation to the image constructed by the OCT imager 250 to identify an image region corresponding to the anterior surface of the crystalline lens. The image region corresponding to the anterior surface of the crystalline lens is referred to as a crystalline lens anterior surface image. The tilt information generator 231 may perform approximation of the identified crystalline lens anterior surface image by a differentiable shape or figure such as a curve or a surface.

Subsequently, the tilt information generator 231 analyzes the crystalline lens anterior surface image (or the crystalline lens image) to identify the apex of the anterior surface of the crystalline lens. For example, the tilt information generator 231 may identify the central position of the crystalline lens anterior surface image and define the identified central position as the apex of the anterior surface of the crystalline lens. Here, the central position of the crystalline lens anterior surface image may be either one of the following points, for example: a point on the crystalline lens anterior surface image that is located equidistantly from both ends of the crystalline lens anterior surface image; or a point on the crystalline lens anterior surface image that has an equal distance along the crystalline lens anterior surface image from both ends of the crystalline lens anterior surface image. In another example, the tilt information generator 231 may identify the apex of the anterior surface of the crystalline lens based on the shape of the crystalline lens anterior surface image. In yet another example, the tilt information generator 231 may identify the apex of the anterior surface of the crystalline lens based on the morphology or form of the crystalline lens image. For example, the tilt information generator 231 may identify the position on the crystalline lens anterior surface image at which the distance from the crystalline lens posterior surface image is maximum with referring to a thickness distribution of the crystalline lens image, and then define the identified position as the apex of the anterior surface of the crystalline lens.

Furthermore, the tilt information generator 231 may calculate the gradient of the crystalline lens anterior surface image at the apex of the anterior surface of the crystalline lens identified, and then define the value of the gradient or a value calculated therefrom as tilt information (tilt angle). The gradient of the crystalline lens anterior surface image at the apex of the anterior surface of the crystalline lens may be, for example, the gradient of the tangent line to the crystalline lens anterior surface image at the apex of the anterior surface of the crystalline lens or the gradient of the tangent line to a differentiable approximate shape or figure of the crystalline lens anterior surface image at the apex of the anterior surface of the crystalline lens, or may be the gradient of the tangent plane (e.g., the gradient of the normal line) to the crystalline lens anterior surface image at the apex of the anterior surface of the crystalline lens or the gradient of the tangent plane (e.g., the gradient of the normal line) to a differentiable approximate shape or figure of the crystalline lens anterior surface image at the apex of the anterior surface of the crystalline lens.

Figure 6A:
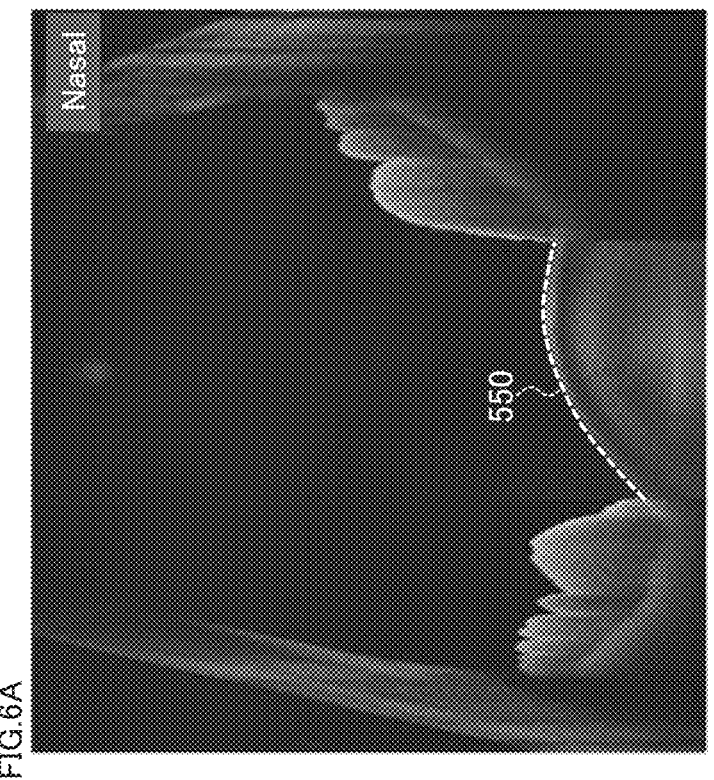
FIG. 6A is a diagram for describing an example of processing executed by an ophthalmic apparatus according to an aspect example.
Figure 6B:
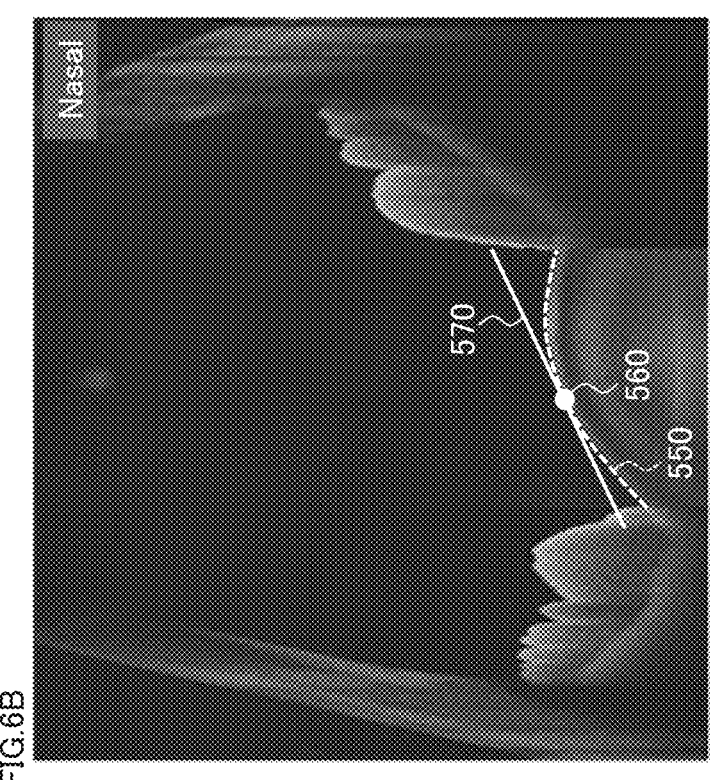
FIG. 6B is a diagram for describing an example of processing executed by an ophthalmic apparatus according to an aspect example.

A specific example in which the feature point is the apex of the anterior surface of the crystalline lens is described below, referring to FIG. 6A and FIG. 6B. To begin with, the tilt information generator 231 identifies the crystalline lens anterior surface image 550 shown in FIG. 6A by applying segmentation to an image obtained by ATA scanning. Here, the tilt information generator 231 may find a differentiable approximate shape or figure of the crystalline lens anterior surface image 550, and then replace the crystalline lens anterior surface image 550 identified by the segmentation with the approximate shape or figure. In the next step, the tilt information generator 231 analyzes the crystalline lens anterior surface image 550 to identify the apex of the anterior surface of the crystalline lens 560. In addition, the tilt information generator 231 calculates the gradient of the tangent line 570 to the crystalline lens anterior surface image 550 at the apex of the anterior surface of the crystalline lens 560, and then sets the value of this gradient (or a value calculated from the gradient) to be a tilt angle. The tilt angle derived in this way is an example of tilt information that represents a tilt state of the anterior eye segment Ea in the case where the ATA scanning of the present example is employed.

An example in which the feature point is the corneal apex (anterior corneal surface apex) is described below. In the present example, the OCT imager 250 applies OCT scanning to a region that includes the corneal apex of the subject's eye E (or the vicinity of the corneal apex). The OCT scanning of the present example may be, for example, a B-scan, a three dimensional scan, or a radial scan. The B-scan of the present example may be, for example, the ATA scan mentioned above. The region to which the three dimensional scan of the present example is applied may be, for example, a volume whose center in the xy direction is placed at the corneal apex or the vicinity thereof. The radial scan (which may be a cross scan) of the present example may include, for example, a plurality of B-scans that have different orientations that intersect at the corneal apex or the vicinity thereof. The OCT imager 250 in the present example then constructs an image from data collected by the OCT scanning of the present example.

The tilt information generator 231 of the present example first analyzes the image constructed by the OCT imager 250 to identify the corneal apex as a feature point. For example, the tilt information generator 231 applies segmentation to the image constructed by the OCT imager 250 to identify an image region corresponding to the anterior surface of the cornea. The image region corresponding to the anterior surface of the cornea is referred to as a corneal anterior surface image. The tilt information generator 231 may perform approximation of the identified corneal anterior surface image by a differentiable shape or figure such as a curve or a surface.

Subsequently, the tilt information generator 231 analyzes the corneal anterior surface image to identify the corneal apex. For example, the tilt information generator 231 may identify the central position of the corneal anterior surface image and define the identified central position as the corneal apex. Here, the central position of the corneal anterior surface image may be either one of the following points, for example: a point on the corneal anterior surface image that is located equidistantly from both ends of the corneal anterior surface image; or a point on the corneal anterior surface image that has an equal distance along the corneal anterior surface image from both ends of the corneal anterior surface image. In another example, the tilt information generator 231 may identify the corneal apex based on the shape of the corneal anterior surface image.

In addition, the tilt information generator 231 may calculate the gradient of the corneal anterior surface image at the corneal apex identified, and then define the value of the gradient or a value calculated therefrom as tilt information (tilt angle). The gradient of the corneal anterior surface image at the corneal apex may be, for example, the gradient of the tangent line to the corneal anterior surface image at the corneal apex or the gradient of the tangent line to a differentiable approximate shape or figure of the corneal anterior surface image at the corneal apex, or may be the gradient of the tangent plane (e.g., the gradient of the normal line) to the corneal anterior surface image at the corneal apex or the gradient of the tangent plane (e.g., the gradient of the normal line) to a differentiable approximate shape or figure of the corneal anterior surface image at the corneal apex.

As described thus far, a series of processes that can be executed in the case where the feature point is the corneal apex may be carried out in the same manner as in the case where the feature point is the apex of the anterior surface of the crystalline lens, for example.

An example in which the feature point is a point on the anterior surface of the iris is described below. In the present example, the OCT imager 250 applies OCT scanning to a region that includes at least part of the anterior surface of the iris of the subject's eye E. The OCT scanning of the present example may be, for example, a B-scan, a three dimensional scan, or a radial scan. The OCT imager 250 in the present example then constructs an image from data collected by the OCT scanning of the present example.

The tilt information generator 231 of the present example first analyzes the image constructed by the OCT imager 250 to identify at least two points on the anterior surface of the iris as feature points. For example, the tilt information generator 231 applies segmentation to the image constructed by the OCT imager 250 to identify an iris anterior surface image. Next, the tilt information generator 231 identifies at least two points in the iris anterior surface image as feature points. Subsequently, the tilt information generator 231 generates tilt information based on the at least two points of the iris anterior surface image identified as feature points. The tilt information generation of the present example may be conducted in the same manner as, for example, but not limited to, any of the first to third examples of the tilt information generation in the case where the feature point is the corner angle.

Figure 7A:
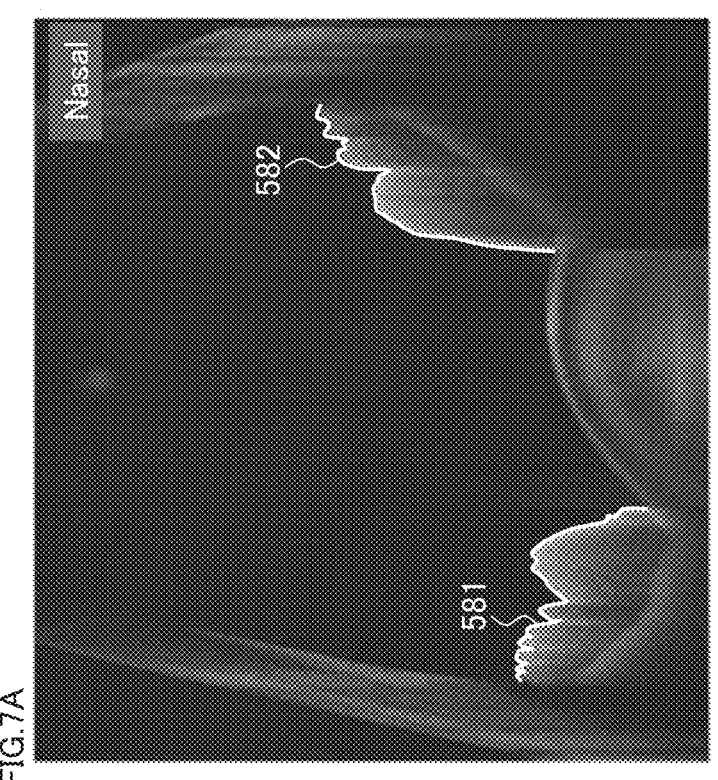
FIG. 7A is a diagram for describing an example of processing executed by an ophthalmic apparatus according to an aspect example.
Figure 7B:
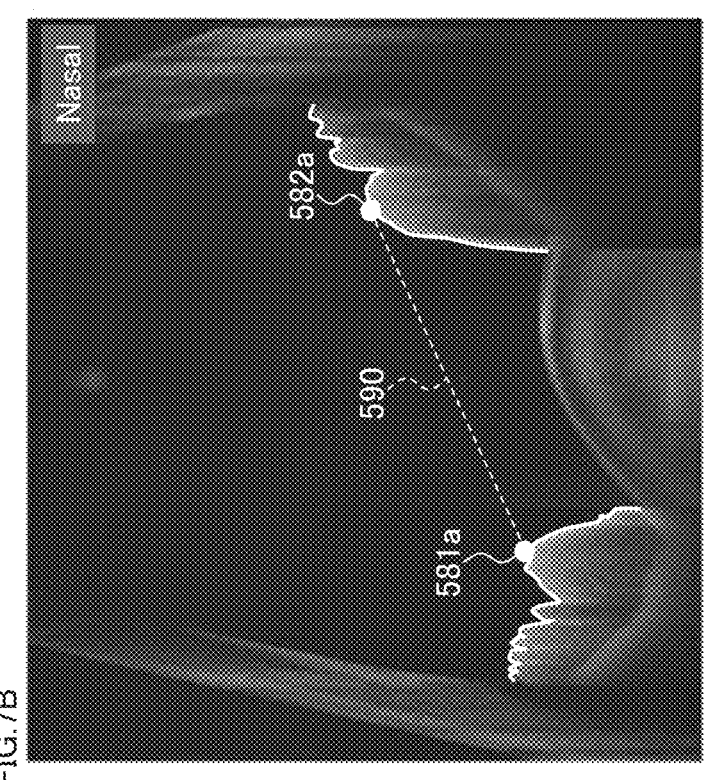
FIG. 7B is a diagram for describing an example of processing executed by an ophthalmic apparatus according to an aspect example.

A specific example in which the feature point is a point on the anterior surface of the iris is described below, referring to FIG. 7A and FIG. 7B. To begin with, the tilt information generator 231 identifies the iris anterior surface images 581 and 582 shown in FIG. 7A by applying segmentation to an image obtained by ATA scanning. The iris anterior surface image 581 is located on the left edge side of the image frame, and the iris anterior surface image 582 is located on the right edge side of the image frame. In the next step, the tilt information generator 231 identifies one or more peaks in the iris anterior surface image 581 and one or more peaks in the iris anterior surface image 582. In the next step, the tilt information generator 231 identifies the peak 581a that is the innermost (the crystalline lens side) among the one or more peaks in the iris anterior surface image 581 and the peak 582a that is the innermost (the crystalline lens side) among the one or more peaks in the iris anterior surface image 582 (see FIG. 7B). Note that other peaks may be identified. In the next step, the tilt information generator 231 calculates the gradient of the straight line 590 that connects the peak 581a and the peak 582a, and then sets the value of this gradient (or a value calculated from the gradient) as a tilt angle (see FIG. 7B). The tilt angle derived in this way is an example of tilt information that represents a tilt state of the anterior eye segment Ea in the case where the corresponding ATA scanning is employed. Instead of obtaining peaks of an iris anterior surface image, any predetermined point in an iris anterior surface image, such as a valley of the iris anterior surface image, the innermost (the crystalline lens side) point of the iris anterior surface image, or the outermost point of the iris anterior surface image, may be used as a feature point.

<Controller 210>

The controller 210 shown in FIG. 4 is configured to perform a control of the LCD 39 (fixation target presenting unit) based on the tilt information generated by the tilt information generator 231. In the present aspect example, the controller 210 performs a control of the LCD 39 to move a fixation target. More specifically, the controller 210 of the present aspect example performs a control of the LCD 39 to change the display position of a fixation target image. Several examples of the fixation target movement control of the present aspect example are described below.

The first example of the fixation target movement control will be described. In the present example, the correspondence information 2121 shown in FIG. 4 is prepared and stored in the memory 212 in advance. Note that the correspondence information 2121 may be arranged outside the controller 210. In some examples, the correspondence information 2121 may be stored in a storage device accessible by the controller 210. The controller 210 (the main controller 211) performs a control of the fixation target presenting unit, with referring to the correspondence information 2121, based on the tilt information generated by the tilt information generator 231.

The correspondence information 2121 is information that represents a correspondence (a relationship) between the following two parameters: a parameter representing a tilt state of an anterior eye segment in an image frame (i.e., in a coordinate system with which an image is defined); and a parameter representing a movement state of a fixation target. Here, the former and the latter parameters are referred to as a tilt parameter and a movement parameter, respectively. For example, based on the tilt information generated by the tilt information generator 231 and a tilt parameter, the main controller 211 determines a corresponding movement parameter, and then performs a control of the fixation target presenting unit based on the movement parameter thus determined.

The tilt parameter of the present example is data that can be compared with the tilt information generated by the tilt information generator 231. For example, the tilt parameter of the present example may be either one of the following tilt angles, for example: a tilt angle defined in the same way as the tilt angle included in the tilt information (the same reference direction is used); or a tilt angle defined using a reference direction (second reference direction) different from the reference direction (first reference direction) of the tilt angle included in the tilt information. On the other hand, the movement parameter of the present example may be defined on the basis of any one or more of: address information (e.g., pixel position) on the display screen of the LCD 39; a movement amount of a fixation target (e.g., the number of pixels, spatial dimensions); and a content of a control for the LCD 39.

The correspondence information 2121 may be created based on any one or more of the following methods or techniques: a preliminary measurement (preparatory measurement) performed using the ophthalmic apparatus 1 or another ophthalmic apparatus; a computer simulation; and a theoretical calculation.

A typical example is described below. The tilt information of the present example includes a tilt angle with respect to the predetermined first reference direction in the image constructed by the OCT imager 250. Further, the tilt parameter of the present example includes a tilt angle with respect to the predetermined second reference direction in an image frame. The first reference direction and the second reference direction may be the same, and may be the z direction or a direction orthogonal thereto, for example. In the case where the first reference direction and the second reference direction are different from each other, both the first reference direction and the second reference direction can be represented with the same coordinate system (e.g., xyz coordinate system). For example, one of the first reference direction and the second reference direction is the z direction and the other is a direction orthogonal to the z direction. Further, the movement parameter of the present example includes a movement amount of a fixation target. Two examples of the correspondence information 2121 in such a case are described below.

The first example of the correspondence information 2121 is described here. The tilt angle included in the tilt parameter of the present example includes a predetermined unit angle with respect to the second reference direction in an image frame. The unit angle is a minimum unit of a tilt angle obtained by the tilt information generator 231, and may be a freely selected or determined value. The unit angle may be, for example, any one of the following angles: 1 degree, 3 degrees, 5 degrees, and 10 degrees. The movement amount included in the movement parameter of the present example includes a movement amount corresponding to the unit angle included in the tilt parameter. This movement amount is referred to as a unit movement amount. The unit movement amount is a movement amount of a fixation target in order to cancel (eliminate, compensate for) a displacement amount of the subject's eye E (the anterior eye segment Ea, a predetermined site of the anterior eye segment Ea) when the tilt angle changes by the unit angle. In other words, the unit movement amount is a movement amount of a fixation target such that the relative position between the subject's eye E and the ophthalmic apparatus 1 (optical system thereof) is substantially the same before and after a change in the tilt angle by the unit angle. The unit movement amount is represented, for example, as the number of pixels of the LCD 39 or information equivalent to this, or a content of a control for the LCD 39. The correspondence information 2121 of the present example may be created, for example, based on a preliminary or preparatory measurement conducted using the ophthalmic apparatus 1 or another ophthalmic apparatus, based on a computer simulation, based on a theoretical calculation, or based at least on two of these three methods or techniques. In the present example, the main controller 211 performs the first arithmetic processing, the second arithmetic processing, and control processing, for example. The first arithmetic processing is performed by dividing the tilt angle calculated by the tilt information generator 231 by the unit angle. The second arithmetic processing is performed by multiplying the value of the quotient derived by the first arithmetic processing (or, multiplying an integer that approximates the value of the quotient) by the unit movement amount. The control processing is performed by controlling the LCD 39 to move a fixation target by the value of the product derived by the second arithmetic processing (or, by an integer that approximates the value of the product). The movement direction of the fixation target may be determined based on the tilt direction determined from the image by the tilt information generator

231. The movement direction of the fixation target is a direction that decreases the tilt angle.

The second example of the correspondence information 2121 is described below. The correspondence information 2121 of the present example includes information that represents a correspondence between: a plurality of different tilt angles with respect to the second reference direction in the image frame; and a plurality of different movement amounts. The correspondence information 2121 of the present example may be represented in any form or mode, and may be a graph, a table, or a list that represents the correspondence between the tilt angles and the movement amounts. The correspondence information 2121 of the present example may be created, for example, based on a preliminary or preparatory measurement performed using the ophthalmic apparatus 1 or another ophthalmic apparatus, based on a computer simulation, based on a theoretical calculation, or based at least on two of these three methods or techniques. In the present example, the main controller 211 performs, for example, the following processes: a process of finding a tilt angle from the correspondence information 2121 corresponding to the tilt angle calculated by the tilt information generator 231 (e.g., a process of identifying a tilt angle in the correspondence information 2121 that is equal to or closest to the tilt angle calculated by the tilt information generator 231); a process of determining a movement amount corresponding to the identified tilt angle from the correspondence information 2121; and a process of controlling the LCD 39 so as to move the fixation target by the movement amount determined. The movement direction of the fixation target is a direction that decreases the tilt angle, and may be determined based on the tilt direction obtained from the image by the tilt information generator 231.

A description will be given of an example of the case in which a tilt direction is taken into consideration. In the present example, the tilt information generator 231 finds a tilt angle and a tilt direction with respect to the first reference direction in an image constructed by the OCT imager 250, and then generates tilt information including both the tilt angle and the tilt direction. Further, the tilt parameter included in the correspondence information 2121 of the present example includes both a tilt angle and a tilt direction with respect to the second reference direction in an image frame. In addition, the movement parameter included in the correspondence information 2121 of the present example includes both a movement amount and a movement direction of a fixation target. The correspondence information 2121 of the present example may be generated, for example, based on a preliminary or preparatory measurement performed using the ophthalmic apparatus 1 or another ophthalmic apparatus, based on a computer simulation, based on a theoretical calculation, or based at least on two of these three methods or techniques. With referring to the correspondence information 2121 configured in this way, the main controller 211 of the present example determines a movement amount of a fixation target based on the tilt angle included in the tilt information generated by the tilt information generator 231 and also determines a movement direction of the fixation target based on the tilt direction included in the tilt information, for example. Furthermore, the main controller 211 controls the LCD 39 in such a manner as to move the fixation target by the determined movement amount in the determined movement direction. This concludes the description of the first example of the fixation target movement control.

Next, the second example of the fixation target movement control will be described. The first example of the fixation target movement control described above is operates to determine the movement amount and/or the movement direction of the fixation target from the tilt state detected. The present example (the second example), on the other hand, operates to search for an appropriate position of the fixation target while monitoring the tilt state. In the present example, the correspondence information 2121 is not necessary. Having said this, however, the present example may also be configured to sequentially determine the movement direction and/or the movement amount while referring to the correspondence information 2121.

The controller 210 (the main controller 211) is configured to perform the following controls in parallel: a control of the LCD 39, a control of the OCT imager 250, and a control of the tilt information generator 231. This parallel (concurrent) control may include, for example, any one or more of a simultaneous control, an alternating control, and a cyclic control.

The control of the LCD 39 in the present example is a control to move the fixation target. The mode of the movement of the fixation target under this control may be a continuous movement, a stepwise movement, or a combination of a continuous movement and a stepwise movement.

The control of the OCT imager 250 in the present example is a control to sequentially construct an image while repetitively applying OCT scanning to the anterior eye segment Ea. The scan pattern used for this repetitive OCT scanning may be freely selected or determined, and may be a B-scan, for example. Such an operation of the OCT imager 250 is referred to as live OCT scanning, real-time OCT moving image photography, OCT video recording, or the like.

The control of the tilt information generator 231 in the present example is a control to sequentially generate tilt information from an image sequentially constructed by the OCT imager 250. This tilt information may include a tilt angle and a tilt direction, for example.

Combining these three controls allows the ophthalmic apparatus 1 to perform OCT moving image photography and tilt information generation in real time while moving the fixation target (thereby, while causing the direction of the line of sight of the subject's eye E to change).

In this combination control, the controller 210 may feed the generated tilt information back to the fixation target movement control. In other words, the controller 210 may determine a movement direction of the fixation target based on any of a plurality pieces of tilt information sequentially generated by the tilt information generator 231 from images sequentially constructed by the OCT imager 250, and then perform a control of the LCD 39 so as to move the fixation target in the movement direction determined in this way. Furthermore, the controller 210 may determine a movement amount of the fixation target based on any of the plurality of pieces of tilt information sequentially generated by the tilt information generator 231 from the images sequentially constructed by the OCT imager 250, and then perform a control of the LCD 39 so as to move the fixation target by the movement amount determined in this way. In addition, by combining these operations, the controller 210 may determine a movement direction and a movement amount of the fixation target based on any of the plurality of tilt information sequentially generated by the tilt information generator 231 from the images sequentially constructed by the OCT imager 250, and then perform a control of the LCD 39 in such a manner as to move the fixation target by the determined movement amount in the determined movement direction. Note that the controller 210 may refer to the correspondence information 2121 in a feedback control as described here.

The controller 210 of the present example is configured to determine whether or not the sequentially generated tilt information satisfies a predetermined condition. This predetermined condition is referred to as a tilt state assessment condition. In a typical example, tilt information includes a tilt angle with respect to a predetermined reference direction in an image. Here, the predetermined reference direction is typically a direction orthogonal to the z direction and more specifically a horizontal direction. If this is the case, the tilt state assessment condition includes a condition related to a tilt angle. For example, the tilt state assessment condition in this case may be that a tilt angle is smaller than a predetermined threshold value. In this case, the controller 210 is configured to determine whether or not a tilt angle sequentially generated by the tilt information generator 231 is equal to or less than the threshold value. In other words, the controller 210 is configured to determine whether or not a tilt direction of the anterior eye segment substantially matches the horizontal direction. This threshold value is set in advance and the magnitude of the threshold value may be freely selected or determined. In some examples, the threshold value may be changed according to the purpose or use of the anterior eye segment OCT image. In a typical example, a threshold value for an anterior eye segment OCT image for analysis use (measurement use) may be set smaller than a threshold value for an anterior eye segment OCT image for observation use.

Furthermore, the controller 210 is configured to perform a control of the LCD 39 to stop a movement of the fixation target in response to a fact that tilt information satisfying the tilt state assessment condition has been obtained. Performing such a control allows a position of the fixation target to be found such that the tilt direction of the anterior eye segment substantially matches the horizontal direction. In other words, an image with almost no tilt of the anterior eye segment can be obtained. This concludes the description of the second example of the fixation target movement control.

<Operation of Ophthalmic Apparatus>

Below, descriptions of several examples of an operation of the ophthalmic apparatus 1 will be given. It is assumed that the same preparatory processes as in a conventional case, such as entering a patient ID and inserting the attachment for anterior eye segment OCT 400 into the sample arm, have already been done.

First Operation Example

Figure 8:
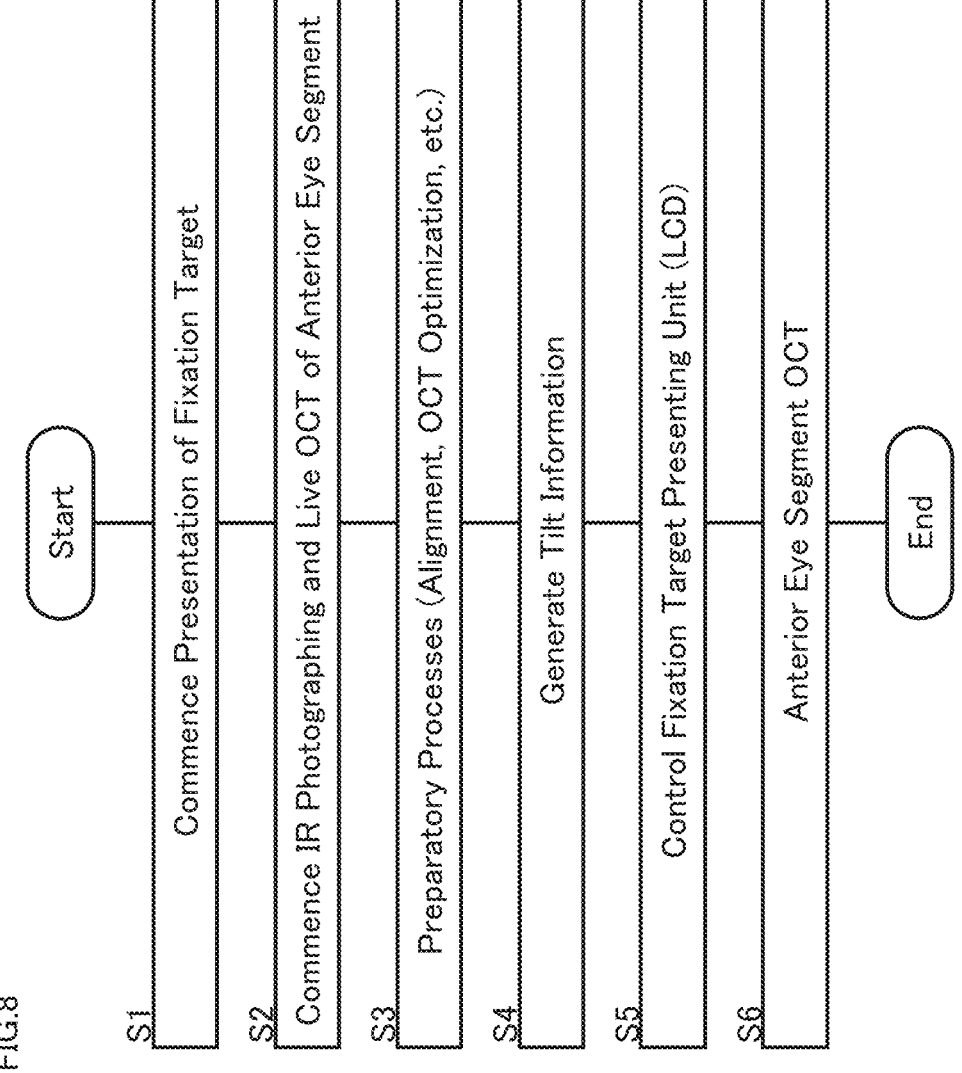
FIG. 8 is a flowchart illustrating an example of an operation of an ophthalmic apparatus according to an aspect example.

The first example of an operation of the ophthalmic apparatus 1 will be described with referring further to FIG. 8. The present example is a fundamental operation example of the ophthalmic apparatus 1.

(S1: Commence Presentation of Fixation Target)

The main controller 211 controls the LCD 39 to present the fixation target to the subject's eye E. The initial display position of the fixation target image may be, for example, the central position of the display screen of the LCD 39.

(S2: Commence Infrared Photographing and Live OCT of Anterior Eye Segment)

Next, the main controller 211 controls the fundus camera unit 2 to commence infrared photographing of the anterior eye segment Ea, and also controls the OCT imager 250 to apply live OCT scanning to the anterior eye segment Ea. The live OCT scanning of the present example may be, for example, repetitive ATA scanning at a predetermined repetition rate.

(S3: Preparatory Processes)

Next, the ophthalmic apparatus 1 performs predetermined preparatory processes with referring to (on the basis of) the infrared observation image and/or the OCT image (B-scan image) of the anterior eye segment Ea, acquisitions of which have started in the step S2. Examples of the preparatory processes may include alignment, focus adjustment, OCT polarization adjustment, and any other known preparatory operations.

(S4: Generate Tilt Information)

After the completion of the preparatory processes, the main controller 211 sends an OCT image acquired by the live OCT scanning started in the step S2 to the tilt information generator 231. In some examples, this OCT image may be a single B-scan image constructed from data collected by a single ATA scan, and more specifically may be the most recent B-scan image. In some other examples, the main controller 211 may send two or more OCT images to the tilt information generator 231.

The tilt information generator 231 analyzes the OCT image provided from the main controller 211 to generate tilt information that represents a tilt state of the anterior eye segment Ea depicted in this OCT image. In the case where two or more OCT images are provided from the main controller 211, the tilt information generator 231 may, for example, perform any of the following processes: a process of generating information that represents a time series change (time dependent change) in tilt information (referred to as time series tilt information); a process of executing a statistical calculation on two or more pieces of tilt information to generate a smaller number of pieces of tilt information (e.g., a single piece of tilt information); a process of selecting a single piece of tilt information from among two or more tilt information; and a process of executing combination processing of any two or more of the above processes.

(S5: Control the Fixation Target Presenting Unit)

Next, the controller 210 performs a control of the LCD 39 based on the tilt information generated in the step S4.

(S6: Anterior Eye Segment OCT)

After the execution of the fixation target control of the step S5, the controller 210 controls the OCT imager 250 to apply OCT scanning to the anterior eye segment Ea in order to acquire an OCT image (for diagnostic use). The execution timing of this OCT scanning may be freely determined. For example, the OCT scanning may be performed immediately after the fixation target control of the step S5, or after execution of one or more steps or processes subsequent to the fixation target control of the step S5. Examples of steps or processes executed subsequently to the fixation target control include checking of a tilt state, assessment or evaluation of a tilt state, display or presentation of information, reception of an operation (instruction), and so forth.

With the present operation example, it becomes possible to apply OCT scanning to the anterior eye segment Ea after conducting a control of the fixation target according to the tilt state of the anterior eye segment Ea depicted in the OCT image, thereby acquiring an OCT image (for diagnostic use). As a result of this, the present operation example makes it possible to perform OCT scanning on the anterior eye segment Ea after conducting adjustment, correction, and/or like operations or processing according to the tilt state of the anterior eye segment Ea, thereby acquiring an OCT image suitable for diagnostic use and/or other purposes.

Second Operation Example

Figure 9:
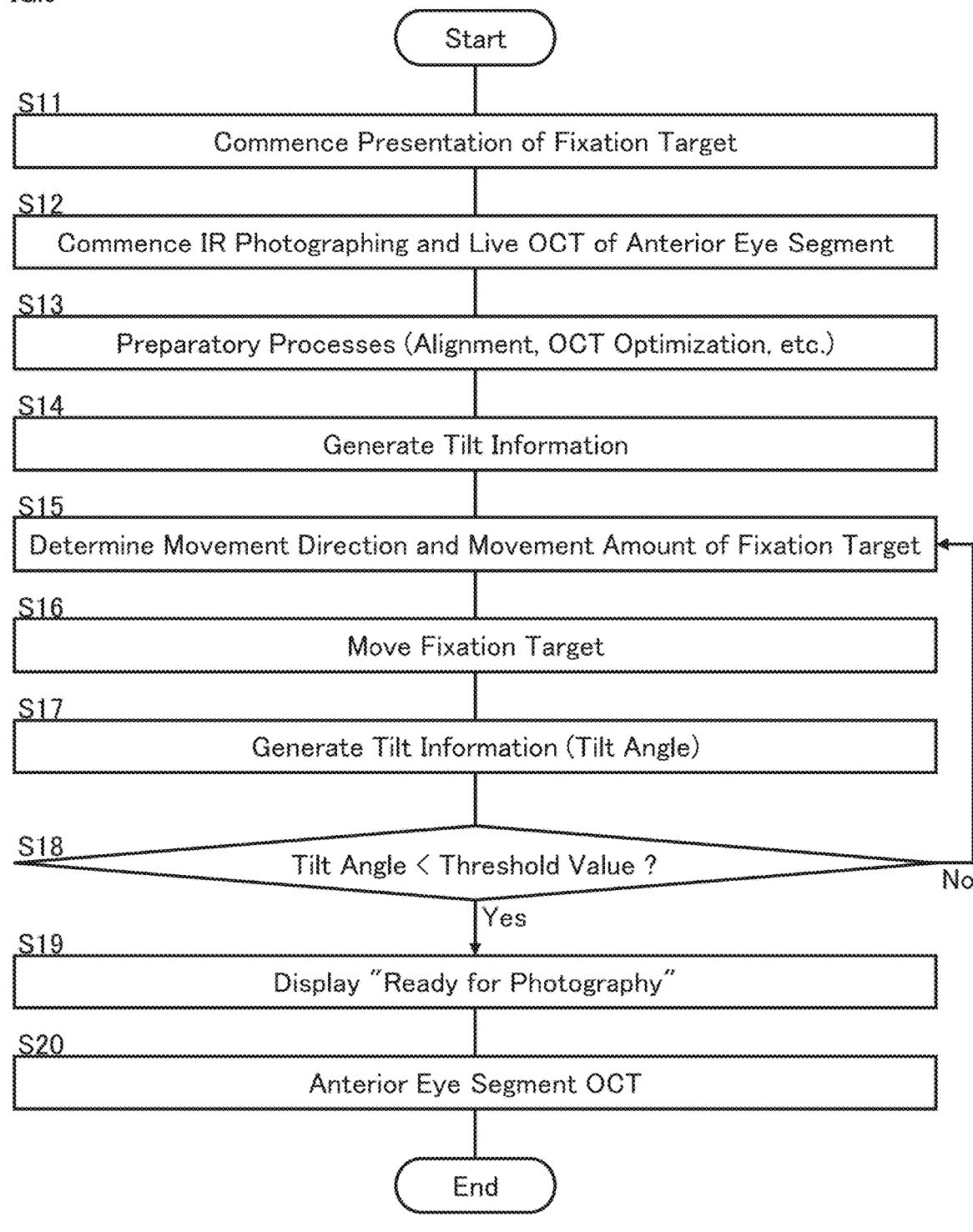
FIG. 9 is a flowchart illustrating an example of an operation of an ophthalmic apparatus according to an aspect example.

The second example of an operation of the ophthalmic apparatus 1 will be described with referring further to FIG. 9. The present example is an example of an operation that can be performed in the case where the above-described first example of the fixation target movement control is employed. The correspondence information 2121 shown in FIG. 4 is stored in the memory 212 in advance.

(S11 to S14)

The steps S11 to S14 may be performed in the same manner as the steps S1 to S4 of the first operation example.

(S15: Determine Movement Direction and Movement Amount of Fixation Target)

The controller 210 determines a movement direction and a movement amount of the fixation target based on the tilt information generated in the step S14 with referring to the correspondence information 2121.

(S16: Move Fixation Target)

The controller 210 moves the fixation target based on the movement direction and the movement amount determined in the step S15. For example, based on the movement direction and the movement amount determined in the step S15, the controller 210 performs a control of the LCD 39 to move the display position of the fixation target image in the movement direction by the movement amount.

Note that the ophthalmic apparatus 1 may be configured to perform anterior eye segment OCT scanning (the step S20) for acquiring an OCT image (for diagnostic use) following the step S16. However, the present operation example is operated to perform the steps S17 to S19 described below in order to ascertain (check, judge, determine) whether or not the position of the fixation target achieved by the step S16 is appropriate.

(S17: Generate Tilt Information)

After the fixation target is moved in the step S16, the controller 210 sends to the tilt information generator 231 an OCT image (B-scan image) newly acquired by the OCT imager 250 that has been performing live OCT scanning. The tilt information generator 231 analyzes this newly acquired OCT image to generate new tilt information (updated tilt information) that represents the tilt state of the anterior eye segment Ea depicted in the newly acquired OCT image. The new tilt information includes at least the tilt angle in the present example.

(S18: Is Tilt Angle Less than Threshold Value?)

The controller 210 compares the tilt angle included in the new tilt information generated in the step S17 with a predetermined threshold value. If the controller 210 determines that the tilt angle is less than the threshold value (S18: Yes), the operation proceeds to the step S19.

On the other hand, if the controller 210 determines that the tilt angle is equal to or greater than the threshold value (S18: No), the operation returns to the step S15. The processes of the steps S15 to S18 are repeatedly executed, for example, until the controller 210 determines in the step S18 that the tilt angle is less than the threshold value (S18: Yes).

In some examples, the controller 210 can repeat the processes of the steps S15 to S18 until a predetermined number of repetitions is reached. The controller 210 can also perform a control of the ophthalmic apparatus 1 so as to stop the operation or to output an error indication (notification that the fixation target cannot be presented at a suitable position) if the number of repetitions has reached the predetermined number. Further, in some examples, the controller 210 can repeat the processes of the steps S15 to S18 until a predetermined operation time length is reached. The controller 210 can also perform a control of the ophthalmic apparatus 1 so as to stop the operation or to output an error indication if the duration of the operation has reached the predetermined time length.

In the present operation example, the operation is returned to the step S15 when it is determined that the tilt angle is equal to or greater than the threshold value (S18: No). In some other operation examples, the operation may be returned to the step S14 when it is determined that the tilt angle is equal to or greater than the threshold value. In other words, the ophthalmic apparatus 1 may be configured to performs the following processes if the tilt angle is determined to be equal to or greater than the threshold value (S18: No): a process of generating new tilt information from an OCT image (B-scan image) newly acquired by the OCT imager 250 that has been performing live OCT scanning (S14); and a process of performing the processes of the steps S15 to S18 again based on the new tilt information.
(S19: Display "Ready for Photography")

When it is determined in the step S18 that the tilt angle is less than the threshold value (S18: Yes), the controller 210 then performs a control of the display device 241 to display information notifying that the fixation target has been presented at an appropriate position and that preparations for photography (anterior eye segment OCT scanning) are complete. Upon recognizing the information displayed, the user may use the operation device 242 to issue an instruction for photography.

It should be noted that, without having to perform the information display and receive the user's instruction operation as described above, the ophthalmic apparatus 1 may be configured to perform photography (anterior eye segment OCT scanning) automatically in response to the determination in the step S18 that the tilt angle is less than the threshold value (S18: Yes). This automatic control is referred to as an automatic shooting function. Note that the ophthalmic apparatus 1 may be configured to perform display of information notifying that preparations for photography have been completed even in the case where the automatic shooting function is employed.
(S20: Anterior Eye Segment OCT)

Upon receipt of an input of the instruction for photography (or when the condition for activating the automatic shooting function is satisfied), the controller 210 controls the OCT imager 250 to apply OCT scanning to the anterior eye segment Ea in order to acquire an OCT image (for diagnostic use). Note that the execution timing of this OCT scanning may be freely selected or determined as in the first operation example.

With the present operation example, as in the first operation example, it becomes possible to apply OCT scanning to the anterior eye segment Ea after conducting a control of the fixation target according to the tilt state of the anterior eye segment Ea depicted in the OCT image, thereby acquiring an OCT image (for diagnostic use). Furthermore, according to the present operation example, the ophthalmic apparatus 1 is capable of automatically determining a movement amount and a movement direction from the tilt state of the anterior eye segment Ea depicted in the OCT image and then moving the fixation target. As a result of this, the ophthalmic apparatus 1 is capable of applying OCT scanning to the anterior eye segment Ea after moving the fixation target to an appropriate position according to the tilt state of the anterior eye segment Ea, making it possible to acquire an OCT image suitable for diagnostic use and/or other purposes. Further, according to the present operation example, after a movement of the fixation target according to the tilt state of the anterior eye segment Ea has been performed, the tilt state after the movement can be checked again. In addition, if the tilt state after the movement is not satisfactory, adjustment or correction of the position of the fixation target can be conducted again.

Third Operation Example

Figure 10:
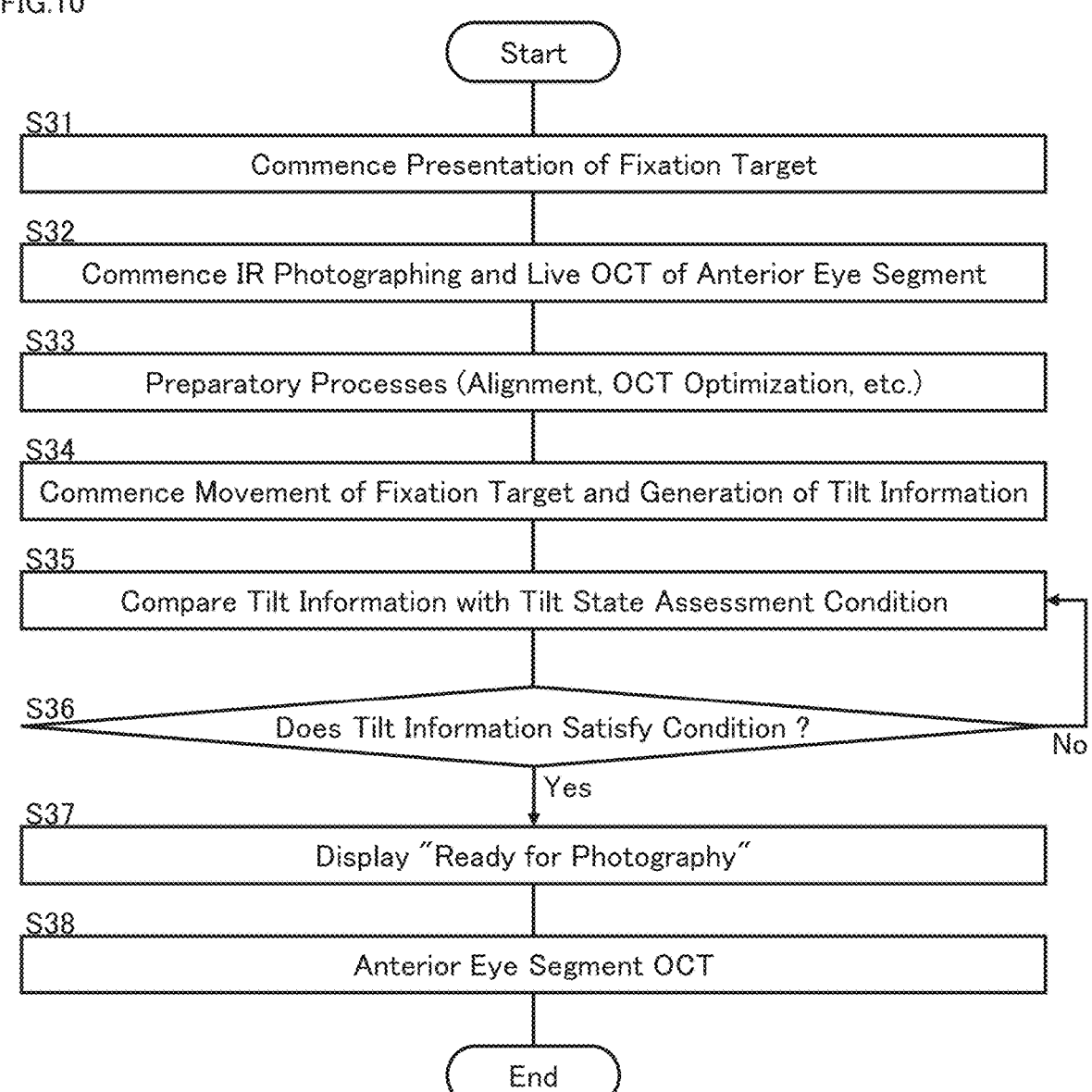
FIG. 10 is a flowchart illustrating an example of an operation of an ophthalmic apparatus according to an aspect example.

The third example of an operation of the ophthalmic apparatus 1 will be described with referring further to FIG. 10. The present example is an example of an operation that can be performed in the case where the above-described second example of the fixation target movement control is employed. As mentioned above, the ophthalmic apparatus 1 may or may not refer to the correspondence information 2121 in the present operation example.
(S31 to S33)

The steps S31 to S33 may be performed in the same manner as the steps S1 to S3 of the first operation example.
(S34: Commence Movement of Fixation Target and Generation of Tilt Information)

The controller 210 commences a control of the LCD 39 to move the fixation target and a control of the tilt information generator 231 to generate tilt information, in addition to the live OCT scanning that has already started in the step S32. As a result of this, the parallel operation of the control of the LCD 39, the control of the OCT imager 250, and the control of the tilt information generator 231 is started.
(S35: Compare Tilt Information with Tilt State Assessment Condition)

The controller 210 compares the tilt information generated by the tilt information generator 231 in the parallel operation started in the step S34 with a tilt state assessment condition determined in advance. For example, the controller 210 compares the tilt angle generated by the tilt information generator 231 in the parallel operation started in the step S34 with a predetermined threshold value.
(S36: Does Tilt Information Satisfy Condition?)

The controller 210 determines whether or not the tilt information satisfies the tilt state assessment condition in the comparison performed in the step S35. For example, controller 210 determines whether or not the tilt angle is less than the threshold value. If the controller 210 determines that the tilt information satisfies the tilt state assessment condition (S36: Yes), the operation proceeds to the step S37.

On the other hand, if the controller 210 determines that the tilt information does not satisfy the tilt state assessment condition (S36: No), the operation returns to the step S35. The parallel operation started in the step S34 is still being performed. The controller 210 compares new tilt information generated by the tilt information generator 231 with the tilt state assessment condition (S35). The processes of the steps S35 and S36 are repeatedly executed, for example, until the controller 210 determines in the step S36 that the tilt information satisfies the tilt state assessment condition (S36: Yes).

In some examples, the controller 210 can repeat the processes of the steps S35 and S36 until a predetermined number of repetitions is reached. The controller 210 can also perform a control of the ophthalmic apparatus 1 so as to stop the operation or to output an error indication (notification that the fixation target cannot be presented at a suitable position) if the number of repetitions has reached the predetermined number. Further, in some examples, the controller 210 can repeat the processes of the steps S35 and S36 until a predetermined operation time length is reached. The controller 210 can also perform a control of the ophthalmic apparatus 1 so as to stop the operation or output an error indication if the duration of the operation has reached the predetermined time length.

(S37: Display "Ready for Photography")

When it is determined in the step S36 that the tilt information satisfies the tilt state assessment condition (S36: Yes), the controller 210 performs a control of the display device 241 to display information notifying that the fixation target has been presented at an appropriate position and that preparations for photography (anterior eye segment OCT scanning) are complete. Upon recognizing the information displayed, the user may use the operation device 242 to issue an instruction for photography.

It should be noted that, without having to perform the information display and the receive the user's instruction operation as described above, the ophthalmic apparatus 1 may be configured to perform photography (anterior eye segment OCT scanning) automatically in response to the determination in the step S36 that the tilt information satisfies the tilt state assessment condition (S36: Yes) (automatic shooting function). Note that the ophthalmic apparatus 1 may be configured to perform display of information notifying that preparations for photography have been completed even in the case where the automatic shooting function is employed.

(S38: Anterior Eye Segment OCT)

Upon receipt of an input of the instruction for photography (or when the condition for activating the automatic shooting function is satisfied), the controller 210 controls the OCT imager 250 to apply OCT scanning to the anterior eye segment Ea in order to acquire an OCT image (for diagnostic use). Note that the execution timing of this OCT scanning may be freely selected or determined as in the first operation example.

With the present operation example, as in the first operation example, it becomes possible to apply OCT scanning to the anterior eye segment Ea after conducting a control of the fixation target according to the tilt state of the anterior eye segment Ea depicted in the OCT image, thereby acquiring an OCT image (for diagnostic use). Furthermore, according to the present operation example, the ophthalmic apparatus 1 is capable of searching for a suitable position (appropriate position) of the fixation target while referring to and monitoring the tilt states of the anterior eye segment Ea depicted in OCT images. Therefore, OCT scanning can be applied to the anterior eye segment Ea after moving the fixation target to an appropriate position according to the tilt state of the anterior eye segment Ea, making it possible to acquire an OCT image suitable for diagnostic use and/or other purposes.

<Combination of Operation Examples>

Any one or more of the steps of the second operation example and any one or more of the steps of the third operation example may be combined. For example, the series of steps S15 to S18 of the second operation example and the series of steps S34 to S36 of the third operation example may be performed in a freely determined order. In some specific examples, these two series of steps may be performed alternately.

<Effects of Ophthalmic Apparatus>

Figure 11:
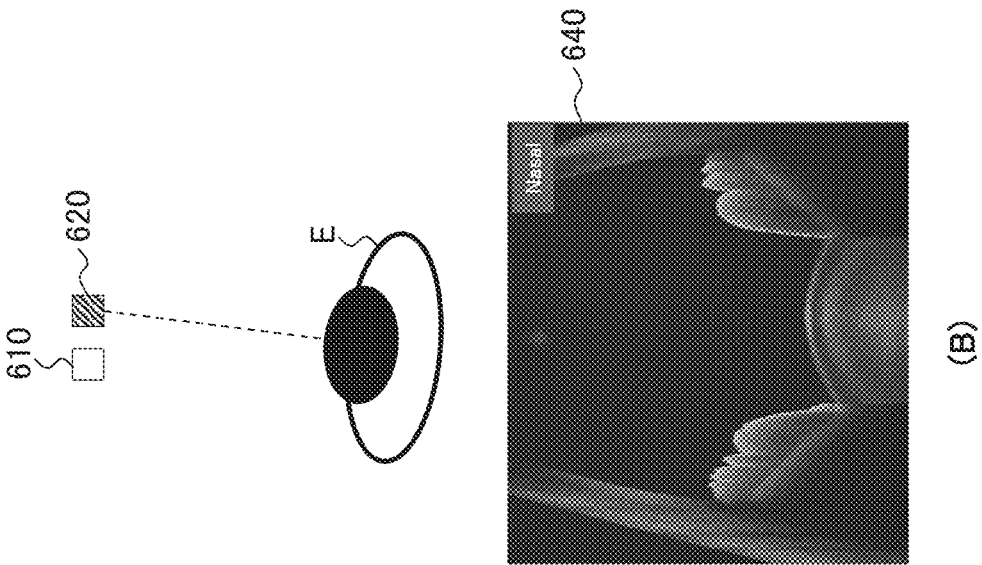
FIG. 11 is a diagram for describing an effect of an ophthalmic apparatus according to an aspect example.
Figure 11:
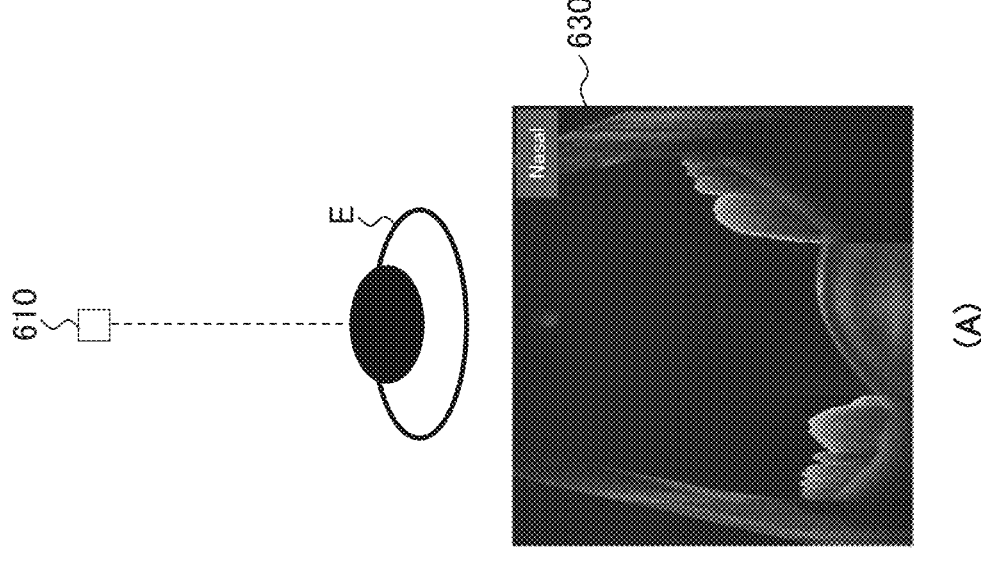

Several effects of the ophthalmic apparatus 1 will be described below. FIG. 11(A) shows a state in which the fixation target 610 arranged at the first position is presented to the subject's eye E. In the anterior eye segment OCT image (an image obtained by ATA scanning) 630 acquired with this fixation target 610 presented, the image of the anterior eye segment Ea is significantly tilted. An anterior eye segment OCT image such as this anterior eye segment OCT image 630 is not suitable for anterior eye segment analysis. For example, with an image like this, parameters such as the distance between two points on the corner angle and the angle of the corner angle cannot be accurately calculated.

When such a problematic situation arises, the ophthalmic apparatus 1 is capable of detecting the tilt state of the image of the anterior eye segment depicted in the anterior eye segment OCT image 630 and then performing a control of the fixation target. By conducting this control of the fixation target, for example, the ophthalmic apparatus 1 is capable of changing the fixation target presented to the subject's eye E from the fixation target 610 placed at the first position shown in FIG. 11(A) to the fixation target 620 placed at the second position shown in FIG. 11(B). As a result of this, the ophthalmic apparatus 1 is capable of change the photography condition from the state shown in FIG. 11(A) in which the anterior eye segment OCT image 630 is obtained to the state shown in FIG. 11(B) in which the anterior eye segment OCT image 640 is obtained. In other words, the ophthalmic apparatus 1 is capable of change the photography condition from the state in which the anterior eye segment OCT image 630 with the image of the anterior eye segment Ea tilted is obtained, to the state in which the anterior eye segment OCT image 640, where the image tilting in the anterior eye segment OCT image 630 is substantially corrected, is obtained. Thus, it becomes possible to accurately conduct anterior eye segment analysis such as corner angle analysis. In this way, the ophthalmic apparatus 1 contributes to the improvement of OCT anterior eye segment analysis.

Other Aspect Examples of Ophthalmic Apparatus

In the aspect examples described thus far, the ophthalmic apparatus 1 is configured to perform an automatic control of the fixation target according to the depiction state (tilt state) of an anterior eye segment in an OCT image. On the other hand, in the aspect example described below, an operation of the fixation target is performed by a user, and the ophthalmic apparatus 1 is configured to offer support and assistance to user's operation according to the depiction state (tilt state) of an anterior eye segment in an OCT image.

Figure 12:
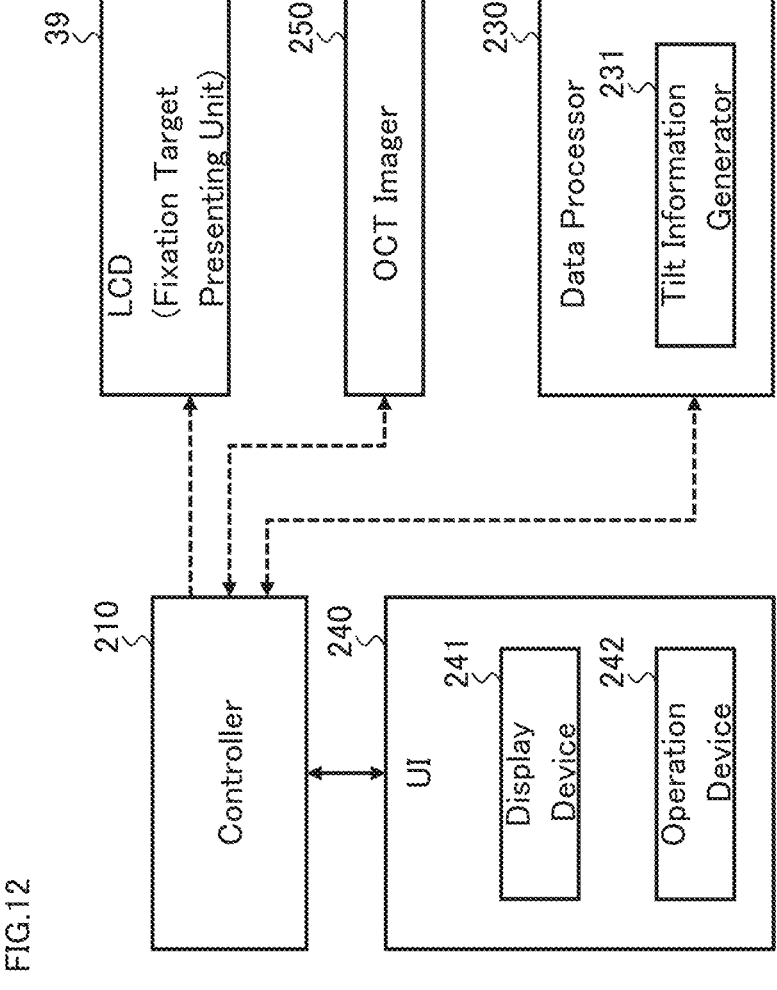
FIG. 12 is a diagram illustrating an example of a configuration of an ophthalmic apparatus according to an aspect example.

The ophthalmic apparatus of the present aspect example may be provided with the same or similar hardware configuration as the ophthalmic apparatus 1 described above. The software configuration may also be the same as or similar to the software configuration of the ophthalmic apparatus 1 described above, except for the software configuration relating to the characteristics and features of the operation of the present aspect example. The ophthalmic apparatus of the present aspect example has the configuration shown in FIG. 1 to FIG. 3, and these drawings will be referred to as needed. Further, in the description of the ophthalmic apparatus of the present aspect example, the configuration shown in FIG. 12 is referred to in place of the configuration shown in FIG. 4. Any matters and items described for the ophthalmic apparatus 1 above can be combined with the ophthalmic apparatus of the present aspect example.

The LCD 39 (fixation target presenting unit) of the ophthalmic apparatus of the present aspect example is configured to present a fixation target to the subject, as with the LCD 39 of the ophthalmic apparatus 1 described above.

The OCT imager 250 of the ophthalmic apparatus of the present aspect example is configured to apply OCT scanning to the anterior eye segment Ea of the subject's eye E and construct an image in the same manner as with the OCT imager 250 of the ophthalmic apparatus 1 described above.

The tilt information generator 231 of the ophthalmic apparatus of the present aspect example, like the tilt information generator 231 of the ophthalmic apparatus 1 described above, is configured to generate tilt information that represents a tilt state of the anterior eye segment Ea depicted in the image constructed by the OCT imager 250.

The operation device 242 of the ophthalmic apparatus of the present aspect example is used for an operation of the fixation target performed by the user, and is configured to generate a signal (fixation target operation signal) upon receipt of this operation.

The controller 210 of the ophthalmic apparatus of the present aspect example is configured to execute a control of the fixation target presenting unit based on the fixation target operation signal from the operation device 242. This control changes the position of the fixation target presented to the subject's eye E. In this way, the user can operate the position of the fixation target.

Furthermore, the controller 210 of the ophthalmic apparatus of the present aspect example is configured to display information on the basis of the tilt information generated by the tilt information generator 231, on the display device 241 (display means). Here, the information displayed on the basis of the tilt information includes information for the user of assisting (supporting) the user's operation of the position of the fixation target.

The information based on the tilt information is, for example, sequentially generated in parallel with live OCT scanning of the anterior eye segment Ea, and displayed together with a live OCT image (real-time moving image) obtained by the live OCT scanning. As a result, the user can observe and grasp the tilt state of the anterior eye segment Ea in the live OCT image in real time. In addition, the user can enjoy assistance and support for operations of the position of the fixation target in order to correct the tilt state of the anterior eye segment Ea.

For example, the information displayed based on the tilt information may include any one or more of information of the following kinds: information representing a tilt angle with respect to a predetermined reference direction in an image of the anterior eye segment Ea acquired by the OCT imager 250 (tilt angle information); information representing a movement amount of the fixation target corresponding to a tilt angle (movement amount information); information representing a tilt direction with respect to a predetermined reference direction in an image of the anterior eye segment Ea acquired by the OCT imager 250 (tilt direction information); and information representing a movement direction of the fixation target corresponding to a tilt direction (movement direction information).

The tilt angle and the tilt direction are obtained by the tilt information generator 231. The tilt angle information may be any kind of display object (e.g., shape or figure, character string, image, etc.) that represents the tilt angle (magnitude of the angle) obtained by the tilt information generator 231. The tilt direction information may be any kind of display object (e.g., shape or figure, character string, image, etc.) that represents the tilt direction (orientation of the tilt) obtained by the tilt information generator 231.

The movement amount information is generated from the tilt angle acquired by the tilt information generator 231. Similarly, the movement direction information is generated from the tilt direction obtained by the tilt information generator 231. The processing of generating other information (e.g., movement amount information, movement direction information, etc.) from the tilt information acquired by the tilt information generator 231 can be executed, for example, with referring to the correspondence information 2121 of the ophthalmic apparatus 1 described above.

In the present aspect example, the display device 241 is an element of the ophthalmic apparatus. However, the display means of another aspect example may not be an element of an ophthalmic apparatus of this another aspect example, but may be, for example, a peripheral device of this ophthalmic apparatus.

According to the ophthalmic apparatus of the present aspect example, the user can be provided with information for the use of assistance and support for operations of the position of the fixation target according to the tilt state of the anterior eye segment Ea depicted in an OCT image. Therefore, the user can easily conduct an operation of correcting the tilt of the anterior eye segment Ea in the OCT image, thereby facilitating the acquisition of an OCT image suitable for diagnostic use and/or other purposes. In this manner, the ophthalmic apparatus of the present aspect example contributes to the improvement of OCT anterior eye segment analysis.

<Control Method of Ophthalmic Apparatus>

Some aspect examples provide a method of controlling an ophthalmic apparatus. The first and second aspects of the control method of an ophthalmic apparatus will be described below. Any matters and items described for the ophthalmic apparatus described above can be combined with the control method.

The first aspect example of the method of controlling an ophthalmic apparatus will be described. The ophthalmic apparatus in the present aspect example includes a fixation target presenting unit, a scanner, and (at least one) processor. The fixation target presenting unit is configured to present a fixation target to a subject, and includes, for example, the LCD 39 described above. The scanner is configured to apply OCT scanning to an anterior eye segment of a subject's eye, and includes, for example, the optical system and mechanisms in the OCT imager 250 described above (the element group forming the sample arm in the fundus camera unit 2, and the OCT unit 100). Given the control method of the present aspect, the processor performs the following three processes.

In the first process, the processor constructs an image based on data collected by the scanner. The processor that performs the first process includes, for example, the image constructing unit 220 described above.

In the second process, the processor generates tilt information that represents a tilt state of the anterior eye segment Ea depicted in the image constructed. The processor that performs the second process includes, for example, the tilt information generator 231 described above.

In the third process, the processor controls the fixation target presenting unit based on the tilt information generated. The processor that performs the third process includes, for example, the controller 210 described above.

The first aspect example configured in this manner makes it possible to apply OCT scanning to the anterior eye segment Ea after controlling the fixation target according to the tilt state of the anterior eye segment Ea depicted in the OCT image and acquire an OCT image (for diagnostic use). Therefore, OCT scanning can be applied to the anterior eye segment Ea after performing adjustment and/or correction according to the tilt state of the anterior eye segment Ea, making it possible to acquire an OCT image suitable for diagnostic use and/or other purposes.

The second aspect example of the method of controlling an ophthalmic apparatus will be described. The ophthalmic apparatus in the present aspect example includes a fixation target presenting unit, a scanner, an operation device, and (at least one) processor. The fixation target presenting unit is configured to present a fixation target to a subject, and includes, for example, the LCD 39 described above. The scanner is configured to apply OCT scanning to an anterior eye segment of a subject's eye, and includes, for example, the optical system and mechanism in the OCT imager 250 described above (the element group forming the sample arm in the fundus camera unit 2, and the OCT unit 100). The operation device is configured to generate a signal upon receipt of an operation and includes, for example, the operation device 242 described above. Given the control method of the present aspect, the processor performs the following four processes.

In the first process, the processor constructs an image based on data collected by the scanner. The processor that performs the first process includes, for example, the image constructing unit 220 described above.

In the second process, the processor generates tilt information that represents a tilt state of the anterior eye segment Ea depicted in the image constructed. The processor that performs the second process includes, for example, the tilt information generator 231 described above.

In the third process, the processor displays information based on the generated tilt information on a display means. A processor that performs the third process includes the controller 210 described above. The display means may be an element of the ophthalmic apparatus, such as the display device 241, or a peripheral device of the ophthalmic apparatus.

In the fourth process, the processor controls the fixation target presenting unit based on the signal from the operation device. The processor that performs the fourth process includes the controller 210 described above.

For example, the user can refer to the information displayed in the third process and perform an operation to move the fixation target. The ophthalmic apparatus moves the fixation target by performing the fourth process upon receipt of this user's operation.

According to the second present aspect example, the user can be provided with information for the use of assistance and support for operations of the position of the fixation target according to the tilt state of the anterior eye segment Ea depicted in an OCT image. Therefore, the user can easily conduct an operation of correcting the tilt of the anterior eye segment Ea in the OCT image, thereby facilitating the acquisition of an OCT image suitable for diagnostic use and/or other purposes.

<Program and Recording Medium>

Some aspect examples provide a program configured to cause a computer (ophthalmic apparatus) to execute the method of controlling an ophthalmic apparatus. In some examples, a program can be created that is configured to cause a computer to execute the first aspect example of the method of controlling an ophthalmic apparatus. In some other examples, a program can be created that is configured to cause a computer to execute the second aspect example of the method of controlling an ophthalmic apparatus. These programs can be combined with any of the matters and items described above for the ophthalmic apparatus.

Some aspect examples provide a computer-readable non-transitory recording medium that retains these programs. For example, some aspect examples provide a computer-readable non-transitory recording medium in which a program configured to cause a computer to execute the first aspect example of the method of controlling an ophthalmic apparatus is recorded. Furthermore, some aspect examples provide a computer-readable non-transitory recording medium in which a program configured to cause a computer to execute the second aspect example of the method of controlling an ophthalmic apparatus is recorded. Any matters and items of the ophthalmic apparatus described above may be incorporated with these recording media. A non-transitory recording medium may be in any form. Examples of this recording medium include a magnetic disk, an optical disk, a magneto-optical disk, a semiconductor memory, and any other kinds of recording media.

While certain embodiments have been described, these embodiments have been presented by way of example only, and are not intended to limit the scope of the inventions. Indeed, the novel embodiments described herein may be embodied in a variety of other forms; furthermore, various omissions, substitutions, additions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ophthalmic apparatus comprising:
   a fixation target presenter including a light source or a liquid crystal display (LCD) and configured to present a fixation target to a subject;
   an OCT imager configured to apply optical coherence tomography (OCT) scanning to an anterior eye segment of a subject's eye to construct an image;
   a tilt information generator configured to generate tilt information that represents a tilt state of the anterior eye segment depicted in the image; and
   a controller configured to
      control the fixation target presenter based on the tilt information,
      control the fixation target presenter to move the fixation target,
      control the fixation target presenter with referring to correspondence information generated in advance that represents correspondence between a tilt parameter representing a tilt state of an anterior eye segment in an image frame and a movement parameter of a fixation target, wherein
   the tilt information includes a tilt angle with respect to a predetermined first reference direction in the image constructed by the OCT imager,
   the tilt parameter includes a tilt angle with respect to a predetermined second reference direction in the image frame, and
   the movement parameter includes a movement amount.

2. The ophthalmic apparatus according to claim 1, wherein
   the tilt angle included in the tilt parameter includes a predetermined unit angle with respect to the second reference direction, and
   the movement amount included in the movement parameter includes a unit movement amount corresponding to the unit angle.

3. The ophthalmic apparatus according to claim 1, wherein the correspondence information includes information that represents correspondence between a plurality of different tilt angles with respect to the second reference direction and a plurality of different movement amounts.

4. The ophthalmic apparatus according to claim 1, wherein the tilt information further includes a tilt direction with respect to the first reference direction, the tilt parameter further includes a tilt direction with respect to the second reference direction, and the movement parameter further includes a movement direction.

5. The ophthalmic apparatus according to claim 1, wherein the controller is configured to perform a control of the fixation target presenter, a control of the OCT imager, and a control of the tilt information generator in parallel, the control of the fixation target presenter being in order to move the fixation target, the control of the OCT imager being in order to sequentially construct an image while repetitively applying OCT scanning to the anterior eye segment, and the control of the tilt information generator being in order to sequentially generate tilt information from the image sequentially constructed by the OCT imager, and the controller is further configured to perform a control of the fixation target presenter to stop a movement of the fixation target in response to generation of tilt information that satisfies a predetermined condition.

6. The ophthalmic apparatus according to claim 5, wherein the condition is a condition related to the tilt angle.

7. The ophthalmic apparatus according to claim 6, wherein the condition is that the tilt angle is smaller than a predetermined threshold value.

8. The ophthalmic apparatus according to claim 5, wherein the controller is configured to perform a control of the fixation target presenter through determining a movement direction of the fixation target based on one or more pieces of the tilt information sequentially generated by the tilt information generator from the image sequentially constructed by the OCT imager.

9. The ophthalmic apparatus according to claim 1, wherein the tilt information generator is configured to analyze the image constructed by the OCT imager to identify at least one feature point and perform generation of the tilt information based on the at least one feature point.

10. The ophthalmic apparatus according to claim 9, wherein the at least one feature point includes one or more of: a corner angle, an apex of an anterior surface of a crystalline lens, a corneal apex, and a point on an anterior surface of an iris.

11. The ophthalmic apparatus according to claim 10, wherein the OCT imager is configured to apply OCT scanning to a region that includes at least two points of the corner angle of the subject's eye and construct the image, and the tilt information generator is configured to identify the at least two points as the feature point and perform generation of the tilt information based on the at least two points.

12. The ophthalmic apparatus according to claim 10, wherein the OCT imager is configured to apply OCT scanning to a region that includes the apex of the anterior surface of the crystalline lens of the subject's eye and construct the image, and the tilt information generator is configured to identify the apex of the anterior surface of the crystalline lens as the feature point, calculate a gradient of the anterior surface of the crystalline lens at the apex of the anterior surface of the crystalline lens, and perform generation of the tilt information based on the gradient.

13. The ophthalmic apparatus according to claim 10, wherein the OCT imager is configured to apply OCT scanning to a region that includes the corneal apex of the subject's eye and construct the image, and the tilt information generator is configured to identify the corneal apex as the feature point, calculate a gradient of an anterior surface of a cornea at the corneal apex, and perform generation of the tilt information based on the gradient.

14. The ophthalmic apparatus according to claim 10, wherein the OCT imager is configured to apply OCT scanning to a region that includes at least part of the anterior surface of the iris of the subject's eye and construct the image, and the tilt information generator is configured to identify at least two points on the anterior surface of the iris as the feature point and perform generation of the tilt information based on the at least two points.

15. A method of controlling an ophthalmic apparatus that includes a fixation target presenter including a light source or a liquid crystal display (LCD) and configured to present a fixation target to a subject, a scanner configured to apply optical coherence tomography (OCT) scanning to an anterior eye segment of a subject's eye, and at least one processor, the method being configured to cause the at least one processor to perform:

constructing an image based on data collected by the scanner;

generating tilt information that represents a tilt state of the anterior eye segment depicted in the image;

controlling the fixation target presenter based on the tilt information;

controlling the fixation target presenter to move the fixation target; and controlling the fixation target presenter with referring to correspondence information generated in advance that represents correspondence between a tilt parameter representing a tilt state of an anterior eye segment in an image frame and a movement parameter of a fixation target, wherein the tilt information includes a tilt angle with respect to a predetermined first reference direction in the image constructed by the OCT imager, the tilt parameter includes a tilt angle with respect to a predetermined second reference direction in the image frame, and the movement parameter includes a movement amount.

16. An ophthalmic apparatus comprising:

a fixation target presenter including a light source or a liquid crystal display (LCD) and configured to present a fixation target to a subject;

an OCT imager configured to apply optical coherence tomography (OCT) scanning to an anterior eye segment of a subject's eye to construct an image;

a tilt information generator configured to generate tilt information that represents a tilt state of the anterior eye segment depicted in the image; and a controller configured to control the fixation target presenter based on the tilt information, wherein the tilt information generator is configured to analyze the image constructed by the OCT imager to identify at least one feature point and perform generation of the tilt information based on the at least one feature point, and wherein the at least one feature point includes one or more of: a corner angle, an apex of an anterior surface of a crystalline lens, a corneal apex, and a point on an anterior surface of an iris.

17. A method of controlling an ophthalmic apparatus that includes a fixation target presenter including a light source or a liquid crystal display (LCD) and configured to present a fixation target to a subject, a scanner configured to apply optical coherence tomography (OCT) scanning to an anterior eye segment of a subject's eye, and at least one processor, the method being configured to cause the at least one processor to perform:

constructing an image based on data collected by the scanner;

generating tilt information that represents a tilt state of the anterior eye segment depicted in the image; and controlling the fixation target presenter based on the tilt information, wherein said generating the tilt information includes analyzing the image constructed by the OCT imager to identify at least one feature point and perform generation of the tilt information based on the at least one feature point, and the at least one feature point includes one or more of: a corner angle, an apex of an anterior surface of a crystalline lens, a corneal apex, and a point on an anterior surface of an iris.

* * * * *